United States Patent [19]

Or et al.

[11] Patent Number: 5,599,927

[45] Date of Patent: Feb. 4, 1997

[54] MACROCYCLIC IMMUNOMODULATORS WITH NOVEL CYCLOHEXYL RING REPLACEMENTS

[75] Inventors: Yat S. Or; Jay R. Luly, both of Libertyville, Ill.

[73] Assignee: Abbott Laboratories, Abbott Park, Ill.

[21] Appl. No.: 573,610

[22] Filed: Dec. 15, 1995

Related U.S. Application Data

[63] Continuation of Ser. No. 334,454, Nov. 8, 1994, abandoned, which is a continuation-in-part of Ser. No. 159,406, Nov. 30, 1993, abandoned.

[51] Int. Cl.⁶ ................... C07D 496/12; A61K 31/33
[52] U.S. Cl. ............................................. 540/456
[58] Field of Search ............................. 540/456

[56] References Cited

U.S. PATENT DOCUMENTS

| | | | |
|---|---|---|---|
| 5,250,728 | 10/1993 | Goulet et al. | 540/456 |
| 5,262,533 | 11/1993 | Sinclair et al. | 540/456 |

FOREIGN PATENT DOCUMENTS

| | | | |
|---|---|---|---|
| 0/428368A1 | 5/1991 | European Pat. Off. | 540/456 |
| 0428365 | 5/1991 | European Pat. Off. | 540/456 |
| 0427680 | 5/1991 | European Pat. Off. | 540/456 |
| 0480623 | 4/1992 | European Pat. Off. | 540/456 |
| 0532089 | 3/1993 | European Pat. Off. | 540/456 |
| 2244991 | 12/1991 | United Kingdom | 540/456 |
| 9113889 | 9/1991 | WIPO | 540/456 |
| WO99/20688 | 11/1992 | WIPO | 540/456 |
| 9305058 | 3/1993 | WIPO | 540/456 |
| 9304680 | 3/1993 | WIPO | 540/456 |
| 9304679 | 3/1993 | WIPO | 540/456 |

OTHER PUBLICATIONS

Schreiber, S. L., et al., "The mechanism of action of Cyclosporin A and FK 506", *Immunology Today*, 13(4): 136–142 (1992).

Hauske, J. R., et al., "Design and Synthesis of Novel FKBP inhibitors", *J. Chem.*, 35(23): 4284–4296 (1992).

Schreiber, S. L., "Chemistry and Biology of the Immunophilins and Their Immunosuppressive Ligands", *Science*, 251: 283–287 (Jan. 1991).

Batchelor, M. J., et al., "Total Synthesis of Close analogues of the Immunosupressant FK 506", *Tetrahedron*, 50(3): 809–826 (1994).

Zimmer, R., et al., "Synthetic Modifications of Asomycin–I. A Chemoselective Removal of the Cyclohexyl Residue of Asomycin", *Tetrahedron*, 50(48): 13655–13670 (1994).

*Primary Examiner*—Robert T. Bond
*Attorney, Agent, or Firm*—Steven R. Crowley; Gregory W. Steele

[57] ABSTRACT

Novel macrolide compounds of the formula

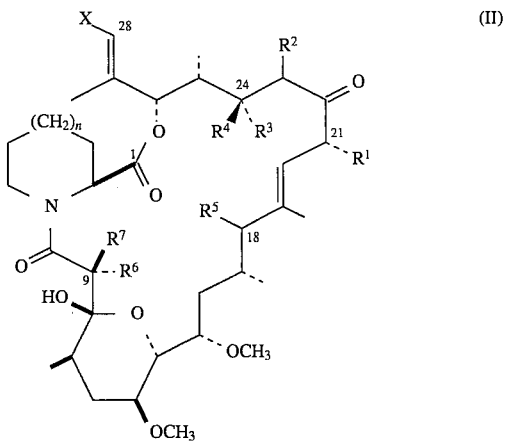

(II)

and pharmaceutically acceptable salts, esters, amides and prodrugs thereof, wherein X is a substituent selected from among radicals having the subformulae

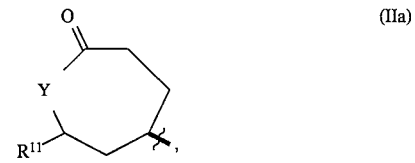

(IIa)

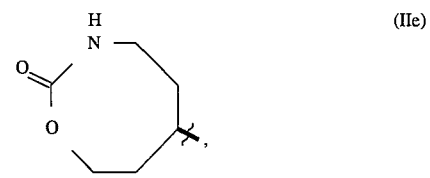

(IIe)

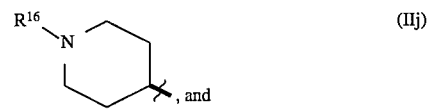

(IIj)

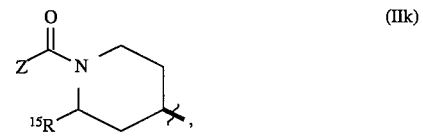

(IIk)

and other heterocyclic radicals, as well as pharmaceutical compositions and methods of immunomodulatory treatment utilizing the same.

6 Claims, No Drawings

MACROCYCLIC IMMUNOMODULATORS WITH NOVEL CYCLOHEXYL RING REPLACEMENTS

This application is a continuation of U.S. patent application Ser. No. 08/334,454, filed Nov. 8, 1994, abandoned, which is a continuation-in-part of U.S. patent application Ser. No. 159,406, filed Nov. 30, 1993, abandoned.

TECHNICAL FIELD

The present invention relates to novel chemical compounds having immunomodulatory activity, and in particular to macrolide immunosuppressants. More particularly, the invention relates to semisynthetic analogs of ascomycin and FK-506, intermediates and processes for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Unsatisfactory side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184,162, published Jun. 11, 1986, disclose a number of macrocyclic compounds isolated from the genus Streptomyces. Immunosuppressant FK-506, isolated from a strain of S. tsukubaensis, is a 23-membered macrocyclic lactone represented by formula 1a, below. Other related natural products, such as FR-900520 (1b) and FR-900523 (1c), which differ from FK-506 in their alkyl substituent at C-21, have been isolated from S. hygroscopicus yakushimnaensis. Yet another analog, FR-900525, produced by S. tsukubaensis, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323,865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

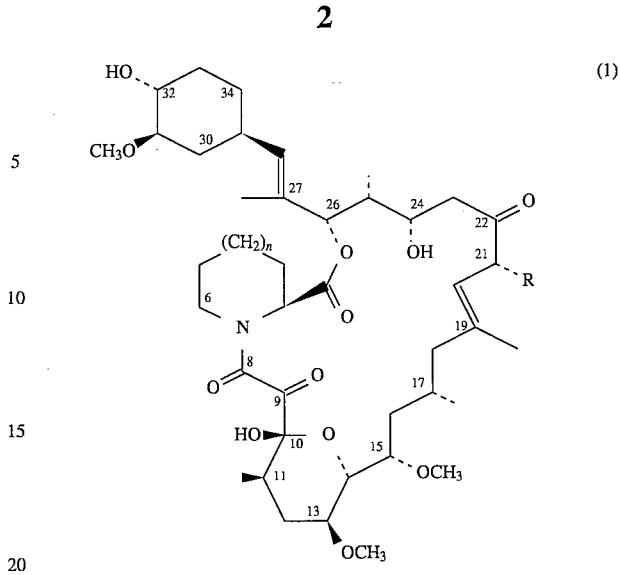

I(a): FK-506 R=$CH_2CH=CH_2$; n=1
I(b): FR-900520 R=$CH_2CH_3$; n=1
I(c): FR-900523 R=$CH_3$; n=1
I(d): FR-900525 R=$CH_2CH=CH_2$; n=0

Fermentation products of FK-type compounds include C-21-epi derivatives of FK-506; a 31-demethylated derivative of FK-506; 31-oxo-FK-506; and compounds derived from FK-506, FR-900523 and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published derivatives include those derived from FK-506 and FR-900520 where the lactone ring is contracted to give a macrocyclic ting containing two fewer carbons.

Several microbial transformations of FK-type compounds at carbon 13 have been published, such as the microbial demethylation of FR-900520 to form the bis-demethylated 13,31-dihydroxy ring-rearranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether formation at C-32 and/or C-24, oxidation of the C-32 alcohol to the ketone, and epoxide formation at C-9.

Although some of these modified compounds exhibit immunosuppressive activity, the need remains for macrocyclic immunosuppressants which do not have the serious side effects frequently associated with immunosuppressant therapy. Accordingly, one object of the invention is to provide novel semisynthetic macrolides which possess the desired immunomodulatory activity but which may be found to minimize untoward side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, at least one of the above compounds. Yet another object of the invention is to provide a method of treating a variety of immune systemrelated disease states, including post-transplant tissue rejection and autoimmune disfunction.

Disclosure of the Invention

In one aspect of the present invention are disclosed compounds having the formula:

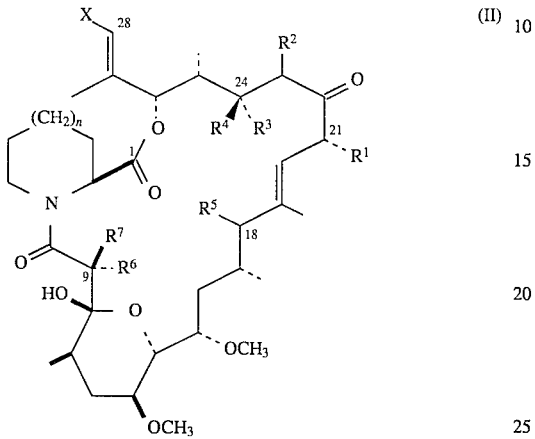 (II)

wherein n is zero or one;

R¹ is selected from the group consisting of methyl, ethyl, propyl, cyclopropylmethyl, 2-oxopropyl, 2-ethanal, 2-hydroxyethyl and allyl;

R² is hydrogen or R² taken together with R³ forms a C-22/C-23 bond;

R³ is selected from the group consisting of hydrogen, hydroxy and protected hydroxy; or R² taken together with R³ forms a C-22/C-23 bond; or R³ taken together with R⁴ is oxo;

R⁴ is hydrogen or R⁴ taken together with R³ is oxo;

R⁵ is selected from hydrogen, hydroxy, protected hydroxy and fluoro;

R⁶ and R⁷ are independently selected from hydrogen, hydroxy and protected hydroxy, with the proviso that at least one of R⁶ and R⁷ is hydrogen; or R⁶ and R⁷ taken together are oxo;

X is a substituent selected from the group of radicals having the following subformulae:

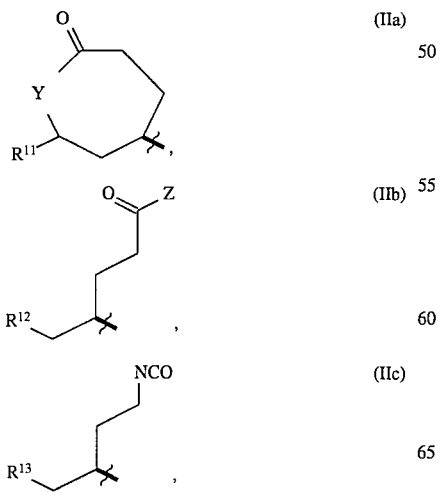

(IIa)

(IIb)

(IIc)

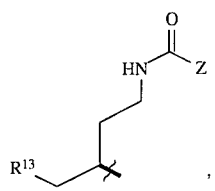 (IId)

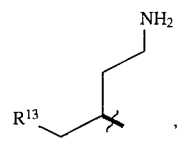 (IId')

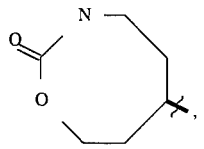 (IIe)

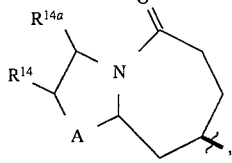 (IIf)

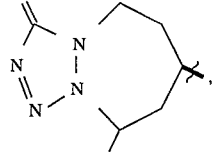 (IIg)

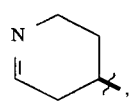 (IIh)

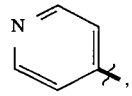 (IIi)

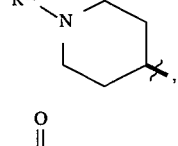 (IIj)

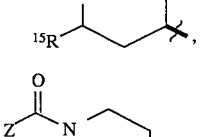 (IIk)

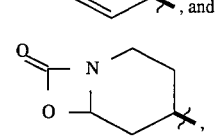 (IIm)

(IIn)

wherein
A is —O— or —S—;

Y is —O— or —NR$^{21}$— wherein R$^{21}$ is selected from the group consisting of:
(1) hydrogen,
(2) —(C1–C10-alkyl) optionally substituted with hydroxy, amino, aryl or heterocyclic,
(3) aryl and
(4) heterocyclic;

Z is selected from the group consisting of hydrogen, hydroxy, —C1–C10-alkyl), aryl, heterocyclic, —(C1–C10-alkoxy) and —NR$^{23}$R$^{24}$, wherein R$^{23}$ and R$^{24}$ are independently selected from:
(1) hydrogen,
(2) aryl,
(3) heterocyclic and
(4) —(C1–C10-alkyl) optionally substituted with hydroxy, amino, aryl or heterocyclic, or, alternatively, —NR$^{23}$R$^{24}$ represents a 3- to 7-membered heterocyclic ring, with the proviso that in subformulae (IId), (IIk) and (IIm) Z is other than hydroxy;

R$^{11}$ is hydrogen, hydroxy or methoxy;

R$^{12}$ is selected from the group consisting of:
(1) —CHO,
(2) —(C1–C10-alkyl) optionally substituted with one, two or three substituents independently selected from the group consisting of hydroxy, amino, aryl and heterocyclic,
(3) —(C2–C10-alkenyl) optionally substituted with aryl or heterocyclic,
(4) —CH$_2$—NR$^{21}$R$^{22}$ where R$^{21}$ is independently defined as above and R$^{22}$ is hydrogen or acyl;

R$^{13}$ is selected from the group consisting of —CHO, hydroxy, protected hydroxy, —(C2–C10-alkenyl) optionally substituted with aryl and —(C1–C10-alkyl) optionally substituted with aryl, with the proviso that in subformula (IId') R$^{13}$ is other than —CHO;

R$^{14}$ and R$^{14}$a are independently selected from hydrogen, aryl, heterocyclic and —(C1–C10-alkyl) or, taken together with the carbon atoms to which they are attached, R$^{14}$ and R$^{14a}$ form an aryl group or a heterocyclic group;

R$^{15}$ is hydrogen or hydroxy; and

R$^{16}$ is selected from the group consisting of
(1) hydrogen,
(2) —(C1–C10-alkyl) optionally substituted with hydroxy, amino, aryl or heterocyclic,
(3) aryl,
(4) heterocyclic and
(5) —C(=NH)—NH$_2$;

or a pharmaceutically acceptable salt, ester, amide or prodrug thereof.

Preferred among the compounds of the present invention are those represented by formula (III):

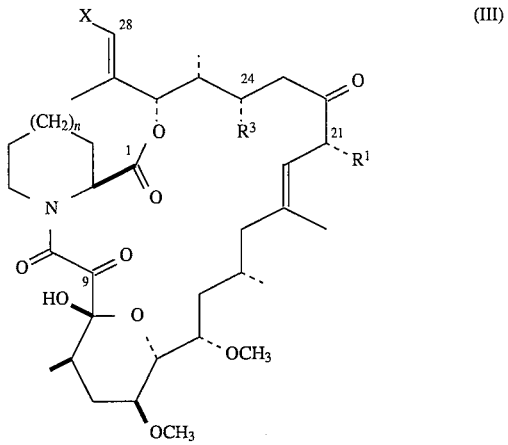

(III)

wherein n is one, R$^1$ and R$^3$ are defined as above and X is a substituent selected from the group of radicals having the following subformulae:

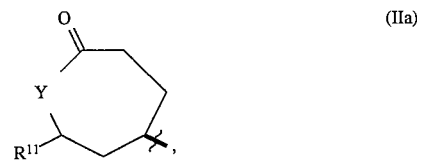

(IIa)

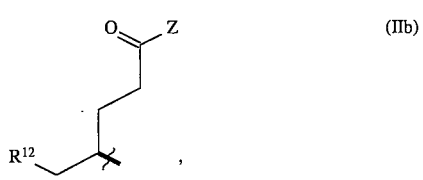

(IIb)

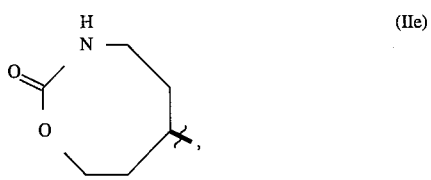

(IIe)

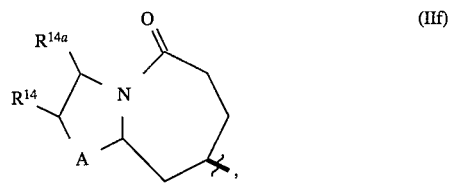

(IIf)

(IIj)

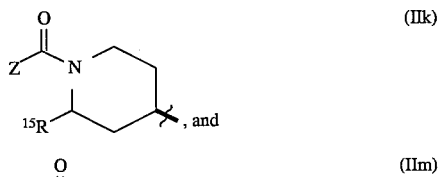

(IIk)

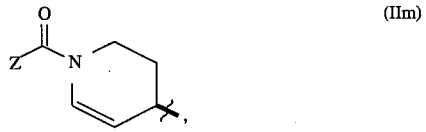

(IIm)

wherein A, Y, Z, $R^{12}$, $R^{14}$, $R^{14a}$ and $R^{16}$ are defined as above and $R^{11}$ and $R^{15}$ are each hydrogen.

Particularly preferred among the compounds of the present invention are those represented by formula III in which n is one and X is a substituent selected from the group of radicals having the following subformulae:

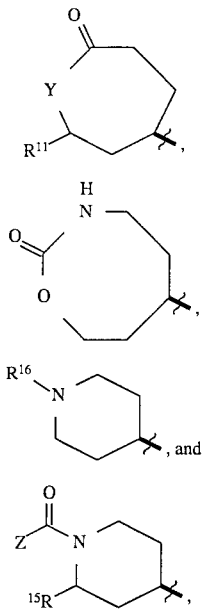

wherein Y, Z and $R^{16}$ are defined as above and $R^{11}$ and $R^{15}$ are each hydrogen.

More particularly preferred among the compounds of the present invention are those represented by formula III in which n is one and X is a substituent selected from the group of radicals having the following subformulae:

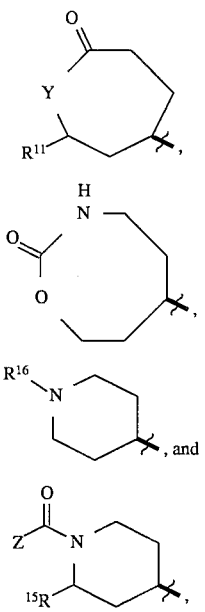

wherein

Y is —O—,

Z is —(C1–C10-alkyl), aryl, heterocyclic or —$NR^{23}R^{24}$, wherein $R^{23}$ and $R^{24}$ are independently selected from:
(1) hydrogen,
(2) aryl,
(3) heterocyclic and (4) —(C1–C10-alkyl) optionally substituted with hydroxy, amino, aryl or heterocyclic, or, alternatively, —$NR^{23}R^{24}$ represents a 3- to 7-membered heterocyclic ring, $R^{16}$ is
(1) hydrogen,
(2) —(C1–C10-alkyl) optionally substituted with hydroxy, amino, aryl or heterocyclic,
(3) aryl or
(4) heterocyclic, and $R^{11}$ and $R^{15}$ are each hydrogen.

Especially preferred, and regarded as the best mode of carrying out the present invention, are the compounds prepared in Examples 11, 37 and 56 (described below).

When examined for immunomodulatory activity using a common in vitro biological assay, the compounds of the invention are seen to be potent immunosuppressant agents. The compounds of this invention possess immunosuppressive, antimicrobial, antifungal, antiviral, antiinflammatory, and antiproliferative activity, as well as the ability to reverse chemotherapeutic drug resistance. Moreover, the compounds of the invention possess the ability to reverse chemotherapeutic drug resistance. As agents which block T-cell activation, a prerequisite for HIV proliferation, the compounds are useful as prophylactics for the prevention of HIV replication. While, the compounds of the invention are useful when used independently of other agents, combination therapy with other immunosuppressants is beneficial as well. These other immunosuppressant agents include but are not limited to FK-506, rapamycin, cyclosporin A, mycophenolic acid, azathioprine, prednisolone, cyclophosphamide, brequinar and leflunomide.

Accordingly, in another aspect of the present invention are disclosed pharmaceutical compositions comprising a compound of the invention in combination with a pharmaceutically acceptable carrier. Suitable carriers and methods of formulation are also disclosed.

In a further aspect of the present invention are disclosed processes for the preparation of the above compounds and synthetic intermediates useful in the preparations of these and other immunomodulator derivatives of ascomycin.

In yet another aspect of the present invention is disclosed a method of immunomodulatory treatment in a human or lower mammal, comprising the administration of a therapeutically effective amount of at least one compound of the invention to a patient in need of such treatment.

Throughout this specification and in the appended claims, the following terms have the meanings specified:

The term "acyl" as used herein refers to —$C(O)R^{30}$ wherein $R^{30}$ is aryl, (C1–C10-alkyl), (C2–C10-alkenyl) or heterocyclic. Examples include, but are not limited to, acetyl, pivaloyl, benzoyl and the like.

The term "C2–C10-alkenyl" as used herein refers to a straight or branched chain group of 2 to 10 carbon atoms containing at least one carbon-carbon double bond including, but not limited to, ethenyl, 1-propenyl, 2-propenyl, 2-methyl-1-propenyl, 1-butenyl, 2-butenyl and the like.

The term "C1–C6-alkoxy" as used herein refers to —$OR^{31}$ wherein $R^{31}$ is (C1–C6-alkyl) including, but not limited to, methoxy, ethoxy, isopropoxy, n-butoxy, sec-butoxy, tert-butoxy and the like.

The term "C1–C10-alkyl" as used herein refers to a monovalent straight chain or branched chain group of 1 to 10 carbon atoms including, but not limited to, methyl, ethyl, n-propyl, isopropyl, n-butyl, sec-butyl, isobutyl, tert-butyl and the like.

The term "C2–C10-alkynyl" as used herein refers to a straight or branched chain group of 2 to 10 carbon atoms containing at least one carbon-carbon triple bond including, but not limited to, propargyl, 1-propynyl, 1-butenyl, 2-butynyl and the like.

The term "aryl", as used herein, refers to mono-, bi- or tricyclic carbocyclic ring system having one or two aromatic rings. Examples of aryl include, but are not limited to, phenyl, 1- or 2-naphthyl, fluorenyl, (1,2)-dihydronaphthyl, (1,2,3,4)-tetrahydronaphthyl, indenyl and the like. Aryl groups can be unsubstituted or substituted with one, two or three substituents independently selected from the group consisting of —(C1-to-C10-alkyl), —(C2-to-C10-alkenyl), halogen, —(CH$_2$)$_m$N(C1–C6-alkyl)$_2$, wherein m is zero to six, —CN, —CHO, mono-, di-, tri-, or perhalogenated —(C1–C6-alkyl), —S(O)$_p$(C1–C6-alkyl), wherein p is 0, 1 or 2, —C(O)N(C1–C6-alkyl), —(CH$_2$)$_m$O(C1–C6-alkyl), where m is as defined above, —(CH$_2$)$_q$OC(O)(C1–C6-alkyl), wherein q is zero to six, —(CH$_2$)$_r$C(O)O(C1–C6-alkyl) wherein r is zero to six, —NO$_2$, —N$_3$, —S(O)$_2$N(C1–C6-alkyl)$_2$, —(C2-to-C10-alkynyl), —C≡C—Si(CH3)3, guanidino, hydroxy,-COOH, -(C1–C6-alkoxy), —OC(O)(C1–C6-alkyl), unsubstituted aryl and unsubstituted Het.

The term "cyclo(C3–C10-alkyl)" as used herein refers to a cyclic group of 3 to 10 carbons including, but not limited to, cyclopropyl, cyclobutyl, cyclopentyl, cyclohexyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ting or a cyclohexane ring or another heterocyclic ring (for example, indolyl, quinolyl, isoquinolyl, tetrahydroquinolyl, benzofuryl, dihydrobenzofuryl or benzothienyl and the like). Heterocyclics include: azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl, cytosinyl, thiocytosinyl, xanthenyl, xanthonyl, uricyl, thyminyl and benzothienyl. Heterocyclics also include compounds of the formula

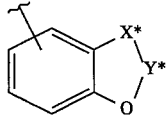

where X* is —CH$_2$— or —O— and Y* is —C(O)— or [—C(R")$_2$—]$_v$, where R" is hydrogen or C$_1$–C$_4$-alkyl and v is 1, 2 or 3 such as 1,3-benzodioxolyl, 1,4-benzodioxanyl and the like.

Heterocyclics can be unsubstituted or monosubstituted or disubstituted with substituents independently selected from —(C1-to-C10-alkyl), —(C2-to-C10-alkenyl), halogen, amino, —(CH$_2$)$_f$N(C1–C6-alkyl)$_2$ wherein f is zero to six, —CN, —CHO, mono-, di-, tri-, or perhalogenated —(C1–C6-alkyl), —S(O)$_g$(C1–C6-alkyl) wherein g is 0, 1 or 2, —C(O)N(C1–C6-alkyl), —(CH$_2$)$_h$O(C1–C6-alkyl) wherein h is 0 to 6, —(CH$_2$)$_i$OC(O)(C1–C6-alkyl) wherein i is 0 to 6, —(CH$_2$)$_j$C(O)O(C1–C6-alkyl) wherein j is 0 to 6, —NO$_2$, —N$_3$, —S(O)$_2$N(C1–C6-alkyl)$_2$, (C2-to-C10-alkynyl), —C≡C—Si(CH$_3$)$_3$, guanidino, hydroxy, —COOH, —(C1–C6-alkoxy), —OC(O)(C1–C6-alkyl), oxo (=O), unsubstituted aryl and unsubstituted Het.

The term "protected hydroxy group" as used herein refers to a hydroxy group which has been protected by a group which is known in the art of organic synthesis to protect a hydroxyl group against undesirable reaction during synthetic procedures and to be selectively removable such as those hydroxy protecting groups disclosed in T. W. Greene and P. G. M. Wuts, Protective Groups in Organic Synthesis, 2nd ed., John Wiley & Son, Inc., 1991, which is hereby incorporated herein by reference. Examples of hydroxy protecting groups include, but are not limited to, substituted methyl ethers, for example, methoxymethyl, methylthiomethyl, 2-methoxyethoxymethyl, benzyloxymethyl, 2-(trimethylsilyl)ethoxymethyl, t-butyl, benzyl and triphenylmethyl; tetrahydropyranyl ethers; substituted ethyl ethers, for example, 2,2,2-trichoroethyl; silyl ethers, for example, dimethylthexylsilyl, trisubstituted silyl such as tris(loweralkyl)silyl (e.g., trimethylsilyl, triethylsilyl, tributylsilyl, tri-isopropylsilyl, tert-butyldimethylsilyl, tri-tert-butylsilyl, triphenylsilyl, triphenylmethyldimethylsilyl, etc.), loweralkyldiarylsilyl (e.g., methyldiphenylsilyl, ethyldiphenylsilyl, propyldiphenylsilyl, tert-butyldiphenylsilyl, etc.), triarylsilyl (e.g., triphenylsilyl, trixylylsilyl, etc.) and triarylalkylsilyl (e.g., tribenzylsilyl, etc.); —C(O)H; —C(O)-loweralkyl (for example, acetyl, propionyl, pivaloyl, t-butylacetyl and the like); —C(O)-aryl (for example, benzoyl and the like); alkoxycarbonyl (for example, ethoxycarbonyl and the like); —S(O)$_2$-(loweralkyl); —S(O)$_2$-(aryl); and the like.

The term "oxo" as used herein refers to (=O).

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgment, suitable for use in contact with the tissues of humans and lower animals without undue toxicity, irritation, allergic response, or the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention, which may be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine, and the like (see, for example S. M. Berge, et al., "Pharmaceutical Salts," *J. Pharm, Sci.*, 66:1–19 (1977)).

Examples of pharmaceutically-acceptable, non-toxic esters of the compounds of this invention include C1-to-C6-alkyl esters wherein the alkyl group is a straight or branched chain. Acceptable esters also include C1-to-C7-cycloalkyl esters as well as arylalkyl esters such as, but not limited to benzyl. C1-to-C4 alkyl esters are preferred. Esters of the compounds of the present invention may be prepared according to conventional methods. Conversely, non-toxic esters of alcoholic moieties on the compounds of the invention may be constructed by condensing these alcohols with C1-to-6-alkyl carboxylic acids, C1-to-C6-alkyl dicarboxylic acids or aryl-carboxylic acids. Examples of such esters include, but are not limited to acetyl, benzoyl or hemisuccinyl.

Examples of pharmaceutically-acceptable, non-toxic amides of the compounds of this invention include amides derived from ammonia, primary C1-to-C6-alkyl amines and secondary di-C1-to-C6-alkyl amines. In the case of secondary amines the amine may also be in the form of a 5-or- 6 membered heterocycle containing one nitrogen atom. Amides derived from ammonia, C1-to-C3-alkyl primary amides and di-C1-to-C2-alkyl secondary amides are preferred. Amides of the compounds of the invention may be prepared according to conventional methods.

"Prodrug" refers to compounds that are rapidly transformed in vivo to yield the parent compound of the above formula, for example, by hydrolysis in blood. A thorough discussion is provided in T. Higuchi and V. Stella, "Prodrugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, which is hereby incorporated herein by reference. Preferred prodrugs include:

(a) acyloxymethyl esters of carboxylic acids, for example, —C(O)—O—CH$_2$—O—C(O)—t—Bu, —C(O)—O—CH(CH$_3$)—O—C(O)—OCH$_2$CH$_3$ or —C(O)—O—Re wherein Re is

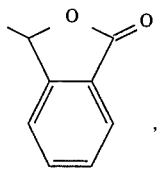

and the like;

(b) (5-methyl-2-oxo-1,3-dioxolen-4-yl)methyl esters of caboxylic acids;

(c) esters derived from alcohol groups in the parent drug by reaction wit succinic acid, phosphoric acid, dialkylaminoacetic acid or an amino acid, for example, —O—C(O)—R$^f$ wherein R$^f$ is (CH$_3$)$_2$NCH$_2$—, NH$_2$CH$_2$—, n—PrNHCH$_2$—, NH$_2$CH$_2$CH$_2$—, (CH$_3$)$_2$NCH$_2$CH$_2$—, (CH$_3$)$_2$NCH$_2$CH$_2$CH$_2$—, N-morpholinylmethyl, N-methyl-N'-piperazinylmethyl, phenyl, CH$_3$CH$_2$CH$_2$—, CH$_3$CH$_2$CH$_2$CH$_2$— or HO(O)CCH$_2$CH$_2$—, and the like;

(d) N-Mannich bases of amides or amines, for example, —C(O)—NH—CH$_2$R$^c$ or —NH—CH$_2$R$^c$ wherein R$^c$ is piperidin-1-yl, morpholin-1-yl, N-phenethylamino, N-phenylpropanolamino, N-methylamino, N-ethylamino, N,N-diethylamino, N,N-dimethylamino, HO(O)C—CH(CH$_3$)—NH—, phenyl-NH— or p—CH$_3$-phenyl-NH—, and the like;

(e) N-hydroxymethyl derivatives of amides, for example, —C(O)—NH—CH$_2$OH;

(f) N-acyloxyalkyl derivatives of amides or heterocyclic amines, for example, —C(O)—NH—Rg or =N-Rg wherein Rg is acetoxymethyl, butyryloxymethyl, benzoyloxymethyl, nicotinoyloxymethyl, N,N-dimethylglycyloxymethyl, N,N-diethylglycyloxymethyl, N,N-dipropylgylcyloxymethyl, phenylalanyloxymethyl, leucyloxymethyl, phenylglycyloxymethyl or N,N-diethylalanyloxymethyl, and the like;

(g) oxazolidinones derived from ketone groups in the parent drug by reaction with 2-aminoethanol, N-methyl-2-aminoethanol, N-(2-hydroxyethyl)-2-aminoethanol, 2-aminopropanol, 2-amino-2-methylpropanol, 2-amino-2-hydroxymethylpropanol, 3-amino-2-hydroxypropane, 2-amino-1-phenylethanol, 3-aminopropanol or N-methyl-2-amino-1-phenylpropanol, and the like; and (h) enol esters derived from ketone groups in the parent drug, for example, acetyl enol esters, propionyl enol esters, butyryl enol esters, isobutyryl enol esters, pivaloyl enol esters, benzoyl enol esters or N,N-dimethylglycyl enol esters, and the like.

Prodrugs of compounds of the present invention may be prepared by any suitable method. For those compounds in which the prodrug moiety is an amino acid or peptide functionality, the condensation of the drug's amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z or Cbz), o-chlorobenzyloxycarbonyl ((2-Cl)Z)), p-nitrobenzyloxycarbonyl (Z(NO$_2$)), p-methoxybenzyloxycarbonyl (Z(OMe)), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt), dimethylphosphino-thioyl (Mpt) and the like.

The examples for protecting groups for carboxyl groups involve, for example, benzyl ester (OBzl), cyclohexyl ester, 4-nitrobenzyl ester (OBzlNO$_2$), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzene-sulfonyl, 4-methoxy- 2,6-dimethyl-benzenesulfonyl (Mts) and the like; the thiol group in cysteine may be protected with benzyl, p-methoxybenzyl, triphenylmethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP) and the like.

As disclosed above, the compounds of the invention are those described by the general formula (II), as well as the pharmaceutically acceptable salts, esters amides and prodrugs thereof. The compounds of the invention are formed by modification of FR-900520 (ascomycin) or one of its congeners (such as FK-506, etc.) by oxidative cleavage at the C-32 position with optional modifications exercised at the C-9, C-18, C-23 and/or C-24 positions. Multiple modifications are also possible by the careful selection of syntheses from those disclosed herein, as by the use of other synthetic methods known to those skilled in the art.

The compounds of the invention may be prepared using one or more processes. The starting materials for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, *FR-900520 and FR-900523, Novel immunosuppressants isolated from A streptomyces. I. Taxonomy of the producing strain. J. Antiblot.*, 1988, XLI(11), 1586–1591; (ii) H. Hatanaka, T. Kino, S. Miyata, N. Inamura, A. Kuroda, T. Goto, H. Tanaka and M. Okuhara, *FR-900520 and FR-900523, Novel immunosuppressants isolated from A streptomyces. II. Fermentation, isolation and physico-chemical and biological characteristics. J. Antiblot.*, 1988, XLI(11 ), 1592–1601; (iii) T. Arai, Y. Koyama, T. Suenaga and H. Honda, *Ascomycin, An Antifungal Antibiotic. J. Antibiot.*, 1962. 15(231–2); and (iv) T. Arai in U.S. Pat. No. 3,244,592. The macrolide FR-900506 (U.S. Pat. No. 4,929,611. issued May 29, 1990), also known as FK-506, may be prepared in accordance to the published methods of Tanaka, Kuroda, and co-workers, *J. Am. Chem. Soc.*, 1987, 109, 5031. One or more of the processes discussed below may be then employed to produce the desired compound of the invention.

Such processes comprise:

(a) producing a compound of formula IIa, where Y is O and $R^{11}$ is —OMe by selective oxidation of a selected —C(=O)—CH(OMe)— group in a corresponding compound;

(b) producing a compound of formula IIa, where Y is O and $R^{11}$ is hydrogen, by recyclization of a compound of formula IIb, where $R^{12}$ is —CH$_2$—OH and Z is OH;

(c) producing a compound of formula IIa, where Y is O and $R^{11}$ is OH (which also exists in the form of formula IIb, where $R^{12}$ is aldehyde and Z is OH) by acid catalyzed ring opening of a compound of formula IIa, where Y is O and $R^{11}$ is —OMe;

(d) producing a compound of formula IIb where $R^{12}$ is $R^{21}$—NH—CH$_2$— by reductive alkylation of a $R^{21}$—NH$_2$ and a compound of formula IIb where $R^{12}$ is —CHO;

(e) producing a compound of formula IIa, where $R^{11}$ is hydrogen and Y is N—$R^{21}$ by cyclic amide formation of a compound of formula IIb, where $R^{12}$ is $R^{21}$—NH—CH$_2$—;

(f) producing a compound of formula lib, where $R^{12}$ is —CH$_2$—OH, by selective reduction of an aldehyde group;

(g) producing a compound of formula IIb, where Z is —NR$^{23}$R$^{24}$ by amide formation of a carboxyl group with an appropriate amine by amide formation reactions;

(h) producing a compound of formula IIc by activation of a —COOH group with azides and Curtis rearrangement of a compound of formula II$_b$;

(i) producing a compound of formula lid where Z is $R^{21}$ by reaction of an isocyanate of a selected compound IIc, with $R^{21}$-CO$_2$H;

(j) producing a compound of formula IId where Z is —(C1–C10-alkoxy) by reaction of an isocyanate of a selected compound IIc with a corresponding alcohol;

(k) producing a compound of formula IId, where Z is NR$^{23}$R$^{24}$ by reaction of an isocyanate of a selected compound IIc with a corresponding amine;

(l) producing a compound of formula IIe by reductive cyclization of an appropriate aldehyde and isocyanate of a selected compound;

(m) producing a compound of formula IIf by reaction of an amino alcohol or thioamino alcohol with a compound of formula IIb, where $R^{12}$ is an aldehyde and Z is —OH, followed by intramolecular amide formation reaction;

(n) producing a compound of formula IIg by reaction of sodium azide with a compound of formula IIc where $R^{13}$ is an aldehyde;

(o) producing a compound of formula IIh by reaction of a compound of formula IIc, where $R^{13}$ is an aldehyde, with hydrofluoric acid;

(p) producing a compound of formula IIi by oxidation of a compound of formula IIh;

(q) producing a compound of formula IIj by reduction of a corresponding cyclic imine IIh;

(r) producing a compound of formula IIm by dehydration reaction of a selected compound of formula IId; and (s) producing a compound of formula IIk by selective hydrogenation of a compound of formula IIm.

In process (a), a suitable reagent for Baeyer-Villiger oxidation is an organic or inorganic peracid such as m-chloroperbenzoic acid, trifluoroperacetic acid, nitro-perbenzoic acid, monopermaleic acid, monoperphthalic acid, peformaic acid or peracetic acid etc. (Krow, G. R. *Organic Reactions*, Vol. 43, pp251–798, John Wiley & Sons, Inc., 1993). The oxidation may be carded in a solvent which does not adversely affect the reaction (e.g. methylene chloride, chloroform, carbon tetrachloride, dichloroethane or chlorobenzene). The reaction may require cooling or heating (0° C. to 100° C.), depending on the method used. Further, the reaction is preferably conducted in the presence of an inorganic base such as cesium carbonate, cesium bicarbonate, potassium carbonate, potassium bicarbonate and the like. The reaction may require 20 minutes to 24 hours to complete, depending on the reagents chosen.

In process (b), a suitable reagent for lactonization is Mukaiyama reagent (Mukaiyama T., *Challenges in Synthetic*

*Organic Chemistry*, p. 118, Clarendon Press, Oxford, 1990), alkyl chloroformate, carbodiimide, diphenylphosphoryl azide or carbonyldiimidazole. The intramolecular cyclization may be carded out in a solvent which does not adversely affect the reaction (e.g. tetrahydrofuran, methylene chloride, chloroform, N,N-dimethylformamide, N-methylpyrrolidone, pyridine or a mixture thereof). The reaction may require cooling or heating, depending on the method used. Further, the reaction is preferably conducted in the presence of an organic or inorganic base such as cesium carbonate, lutidine, picoline, quinoline, diisopropylethylamine and the like. The reaction temperature is preferably from −30° C. to 60° C. The reaction may require 20 minutes to 24 hours to complete, depending on the reagent used.

In process (c), a suitable acid catalyst is p-toluenesulfonic acid, methanesulfonic acid, trifluoroacetic acid, fluorosulfonic acid, hydrofluoric acid, hydrochloric acid, formic acid, acetic acid and the like. The reaction may be carded out in acetone, acetaldehyde, diethylketone, n-butaldehyde and the like. The reaction may require cooling or heating, depending on the method used.

In process (d), a suitable reducing agent is trialkylsilane such as triethylsilane, hydrogen in the presence of catalyst, sodium cyanoborohydride and the like. The reaction may be carded in a solvent which does not adversely affect the reaction (e.g. tetrahydrofuran, N,N-dimethylformamide, N-methylpyrrolidone, formic acid, acetic acid or a mixture thereof). The reaction may require cooling or heating, depend on the reagents used. Further, the reaction is preferably conducted in the presence of amine, $R^{21}$—$NH_2$, in the presence of an organic acid such as formic acid, acetic acid, trifluoroacetic acid and the like.

In process (e), a suitable reagent for lactamization is Mukaiyama reagent (Mukaiyama T., *Challenges in Synthetic Organic Chemistry*, p. 118, Clarendon Press, Oxford, 1990), alkyl chloroformate, carbodiimide, diphenylphosphoryl azide or carbonyldiimidazole. The intramolecular cyclization may be carded out in a solvent which does not adversely affect the reaction (e.g. tetrahydrofuran, methylene chloride, chloroform, N,N-dimethylformamide, N-methylpyrrolidone, pyridine or a mixture thereof). The reaction may require cooling or heating, depending on the method used. Further, the reaction is preferably conducted in the presence of an organic or inorganic base such as cesium carbonate, lutidine, picoline, quinoline, diisopropylethylamine and the like. The reaction temperature is preferably from −30° C. to 60° C. The reaction may require 20 minutes to 24 hours to complete, depending on the reagent used.

In process (f), a suitable reducing reagent is sodium borohydride, sodium cyanoborohydride, lithium triacetoxyborohydride, L-selectride and the like. The reaction may be carried out in a solvent which does not adversely affect the reaction (e.g. diethyl ether, tetrahydrofuran, N,N-dimethylformamide or a mixture thereof). The reaction temperature is preferably from −78° C. to 40° C. The reaction may require 20 minutes to 24 hours to complete, depending on the reagent used.

In process (g), the condensation of the amino group with carboxylic acid may be affected in accordance with conventional condensation methods such as the azide method, the mixed acid anhydride method, the carbodiimide method, the active ester method (p-nitrophenyl ester method, N-hydroxysuccinic acid imide ester method, cyanomethyl ester method and the like), the Woodward reagent K method, the DCC-HOBt (dichlohexylcarbodiimide-1-hydroxybenzotriazole), Mukaiyama method and the like. Classical methods for amide bond formation reactions are described in "Peptide Synthesis: Second Edition, M.Bodansky, Y. S. Klausner and M. A. Ondetti, 1976).

In process (h), the carboxylic acid group is first activated with chloroformate and converted to acyl azide with sodium azide. Alternatively, the carboxylic acid is directly converted to acyl azide using diphenylphosphoryl azide. The acyl azide may be used in Curtius rearrangement with or without further purification. The prefered solvent for the acyl azide formation is acetone-water, tetrahydrofuran-water, dioxane-water, tetrahydrofuran, dichloromethane, chloroform, chlorobenzene and the like. The Curtius rearrangement reaction may be carried in a solvent which does not adversely affect the reaction (e.g. toluene, tetrahydrofuran, dioxane, chloroform or a mixture thereof). The reaction temperature is preferably from 25° C. to 100° C. The reaction may require 20 minutes to 24 hours to complete, depending on the reagent chosen.

In process (i), the carboxylic acid, $R^{21}$—COOH, is directly reacted with the isocyanate in a solvent which does not adversely affect the reaction (e.g toluene, chlorobenzene, chloroform, methylene chloride or a mixture thereof). The reaction temperature is preferably from 25° C. to 100° C. The reaction may require 20 minutes to 24 hours to complete, depending on the reagent chosen.

In process (j), the alcohol, (C1–C10-alkyl) alcohol, is directly reacted with the isocyanate in a solvent which does not adversely affect the reaction (e.g toluene, chlorobenzene, chloroform, methylene chloride or a mixture thereof). The reaction temperature is preferably from 25° C. to 100° C. Further, the reaction is carded out in the presence of organic base such as diisopropylethylamine, triethylamine, pyridine, lutidine and the like. The reaction may require 20 minutes to 24 hours to complete, depending on the reagent chosen.

In process (k), the amine, $R^{23}R^{24}NH$ is directly reacted with the isocyanate in a solvent which does not adversely affect the reaction (e.g toluene, chlorobenzene, chloroform, methylene chloride or a mixture thereof). The reaction temperature is preferably from 25° C. to 100° C. Further, the reaction is carded out in the presence of organic base such as diisopropylethylamine, triethylamine, pyridine, lutidine and the like. The reaction may require 20 minutes to 24 hours to complete, depending on the reagent chosen.

In process (1), a suitable reducing reagent is sodium borohydride, sodium cyanoborohydride, lithium triacetoxyborohydride, L-selectride and the like. The reaction may be carded out in a solvent which does not adversely affect the reaction (e.g. diethyl ether, tetrahydrofuran, N,N-dimethylformamide or a mixture thereof). The reaction temperature is preferably from −78° C. to 40° C. The reaction may require 20 minutes to 24 hours to complete, depending on the reagent used.

In process (m), an amino alcohol or thioamino alcohol is reacted directly with a compound of subformula IIb ($R^{12}$ is —CHO, Z is —OH) in the presence of a drying agent. The reaction may be carded in a solvent which does not adversely affect the reaction (e.g. tetrahydrofuran, chloroform, dichlorethane, methylene chloride, chlorobenzene, toluene, benzene or a mixture thereof). Suitable solid drying agents are powdered anhydrous magnesium surfate, molecular sieves and the like. The intermediate is then cyclized by a standard amide bond formation reaction. The condensation of the amino group with carboxylic acid may be affected in accordance with conventional condensation methods such as the azide method, the mixed acid anhydride method, the carbodiimide method, the active ester method (p-nitrophenyl ester method, N-hydroxysuccinic acid imide ester method, cyanomethyl ester method and the like), the Woodward reagent K method, the DCC-HOBt (dichlohexylcarbodiimide-1-hydroxybenzothiazole), Mukaiyama method and the like. Classical methods for amide bond formation reactions are described in "Peptide Synthesis: Second Edition, M.Bodansky, Y. S.Klausner and M. A. Ondetti, 1976).

In process (n), the carboxylic acid group is first activated with chloroformate and converted to acyl azide with excess sodium azide. Alternatively, the carboxylic acid is directly converted to acyl azide using excess diphenylphosphoryl azide. The acyl azide may be used in Curtius rearrangement followed by cyclization reaction without further purification. The prefered solvent for the acyl azide formation is acetone-water, tetrahydrofuran-water, dioxane-water, tetrahydrofuran, dichloromethane, chloroform, chlorobenzene and the like. The Curtius rearrangement reaction may be carded in a solvent which does not adversely affect the reaction (e.g. toluene, tetrahydrofuran, dioxane, chloroform or a mixture thereof). The reaction temperature is preferably from 25° C. to 100° C. The reaction may require 20 minutes to 24 hours to complete, depending on the reagent chosen.

In process (o), a compound of subformulae IIc ($R^{13}$ is —CHO) is reacted with one to five equivalents of 48% hydrofluoric acid in a solvent which does not adversely affect the reaction (e.g. tetrahydrofuran, acetonitrile, acetone, dioxane or a mixture thereof). The reaction temperature is preferably −78° to 0° C. The reaction may require 1 to 24 hours to complete. At the end of the reaction, the hydrofluoric acid is neutralized by an inorgnic base such as cesium carbonate, cesium bicarbonate, potassium bicarbonate and the like.

In process (p), a suitable catalyst for aromatization is palladium on carbon or platinum. A suitable oxidizing agent is air, oxygen, an olefin and the like. The reaction is preferably carried out in a solvent which does not adversely affect the reaction (e.g. tetrahydrofuran, acetone, diethyl ether, dioxane or a mixture thereof). The reaction may take 1 to 14 days to complete, depending on the conditions chosen.

In process (q), a suitable reducing agent is trialkylsilane such as triethylsilane, hydrogen in the presence of catalyst, sodium cyanoborohydride and the like. The reaction may be carded in a solvent which does not adversely affect the reaction (e.g. tetrahydrofuran, N,N-dimethylformamide, N-methylpyrrolidone, formic acid, acetic acid or a mixture thereof). The reaction may require cooling or heating, depend on the reagents used. Further, the reaction is preferably conducted in the presence of amine, $R^{21}$—$NH_2$, in the presence of an organic acid such as formic acid, acetic acid, trifluoroacetic acid and the like.

In process (r), a compound of subformula IId ($R^{13}$ is —CHO), is activated with methanesulfonyl chloride, trifluoromethanesulfonyl anhydride, fluorosulfonyl anhydride and the like in the presence of an organic base. The preferred organic base is tri-alkyl amine such as triethylamine, diisopropylethylamine, pyridine, lutidine and the like. The dehydration reaction is preferably carried in a solvent which does not adversely affect the reaction (e.g. methylene chloride, chloroform, dichloroethane, chlorobenzene or a mixture thereof). The reaction may require cooling or heating, depending on the conditions used.

In process (s), a suitable reducing agent is trialkylsilane such as triethylsilane, hydrogen in the presence of catalyst, sodium cyanoborohydride and the like. The reaction may be carded in a solvent which does not adversely affect the reaction (e.g. tetrahydrofuran, N,N-dimethylformamide, N-methylpyrrolidone, formic acid, acetic acid or a mixture thereof). The reaction may require cooling or heating, depend on the reagents used. Further, the reaction is preferably conducted in the presence of amine, R21—$NH_2$, in the presence of an organic acid such as formic acid, acetic acid, trifluoroacetic acid and the like.

It should be noted that numerous asymmetric centers may exist in the compounds of the present invention. Except where otherwise specified, the present invention contemplates the various stereoisomers and mixtures thereof. It should also be noted that certain variable elements of the structural formulae herein, such as the radical $R^{21}$ or the subscript integers m and s, may appear more than once in a particular formula. In such instances, it is intended that, within a single formula, the values of these variables may be the same or different at each occurrence.

The present invention can be illustrated by the following non-limiting, representative examples.

EXAMPLE 1

Formula IIa: n=1; $R^1$=Et; $R^2$=H; $R^3$=OH; $R^4$=H; $R^5$=H; $R^6$ and $R^7$ taken together =O; Y=O; $R^{11}$=$OCH_3$,

Example 1a

Formula I(b): n=1; R=—$CH_2CH_3$; 24, 32-Bis-tert-butyldimethylsiloxyascomycin.

A solution of imidazole (41.4 g) in N,N-dimethylformamide (200 mL) was added dropwise into a stirred solution of ascomycin (60 g) and tert-butyldimethylsilyl chloride (91.7 g) in N,N-dimethylformamide (200 mL) at 0° C. After being stirred at 0° C. for 2 hours, the reaction mixture was stirred at room temperature for 48 hours. N,N-dimethylformamide and excess tert-butyldimethylsilyl chloride was removed by distillation under high vacuum. The bath temperature was kept below 35° C. during the distillation. The residue was partitioned between ether (250 mL) and water (400 mL). The aqueous phase was extracted with ether (3×150 mL). The combined organic phase was washed with 1N hydrochloric acid (3×150 mL), brine (300 mL), dried over magnesium surfate and solvent remove in vacuo. The product was purified by silica gel chromatography (1.25 kg) eluting with 12% acetone in hexanes. Yield: 70.3 g; MS (FAB) m/z: M+H=1022.

Example 1b

Formula I(b): n=1; R=—$CH_2CH_3$; 24-tert-Butyldimethylsiloxy-ascomycin.

A solution of hydrofluoric acid (0.5 mL of 48% hydrofluoric acid in 10 mL of acetonitrile) was added dropwise into a solution of the title compound of Example 1(a) (16 g) in acetonitrile (50 mL) at 0° C. After being stirred at this temperature for an additional 15 minutes, the cooling bath was removed and the reaction mixture was stirred at room temperature for 1 hour. The reaction mixture was cooled to 0° C. and powdered sodium bicarbonate (5 g) was added followed by powdered magnesium sulfate (10 g). After being stirred at 0° C. for 1 hour, solids were filtered off and solvent removed in vacuo. The residue was purified by silica gel chromatography (15 g) eluting ether. The crude product was further purified by silica gel chromatography (100 g)

eluting with 10% acetone in hexanes. Yield: 12.3 g; MS (FAB) m/z: M+K=944.

Example 1c

Formula I(b): n=1; R=—CH$_2$CH$_3$; 24-tert-Butyldimethylsiloxy-32-desoxy-32-oxo-ascomycin.

Dimethylsulfoxide (3.26 mL) was added into a stirred solution of oxalyl chloride (3.5 g) in dry methylene chloride (20 mL) at −78° C. under nitrogen. After being stirred at −78° C. for 0.5 hour, a solution of the title compound of Example 1(b) (8.3 g) in dry methylene chloride (30 mL) was added dropwise and stirred at this temperature for an additional 0.5 hour. Triethylamine (9 mL) in methylene chloride (30 mL) was added dropwise into the reaction mixture at −78° C. The cooling bath was removed after the addition and the reaction mixture stirred at room temperature for 0.5 hour. Anhydrous ether (200 mL) was added into the reaction mixture and precipitations filtered off. The solids was triturated with more ether (200 mL). The combined filtrate was washed once with 1N hydrochloric acid, brine, dried over magnesium sulfate and solvent removed in vacuo. The product was purified by silica gel chromatography (50 g) eluting with 10% acetone/hexanes followed by 20% acetone/hexanes. Yield: 7.7 g; MS (FAB) m/z: M+K=942.

Example 1d

Formula I(b): n=1; R=—CH$_2$CH$_3$; 32-desoxy-32-oxo-ascomycin.

The title compound was prepared from the title compound of Example 1(c) (6 g) and hydrofluoric acid in acetonitrile according to the procedure described in Example 1(b). Yield: 5.0 g; MS (FAB) m/z: M+H=790.

Example 1e

Formula IIa: n=1; R$^1$=Et; R$^2$=H; R$^3$=OH; R$^4$=H; R$^5$=H; R$^6$ and R$^7$ taken together=O; Y=O; R$^{11}$=OCH$_3$.

Cesium carbonate (powdered, 15.5 g) was added into a stirred solution of the title compound of Example 1(d) (9.5 g) in dichloromethane (100 mL) at 0° C. m-Chloroperbenzoic acid (5.6 g, 50%) was added portionwise into the stirred suspension over 10 minutes. After being stirred at 0° C. for two hours, the solids were removed by filtration. The filtrate was partitioned between ethyl acetate and saturated sodium bicarbonate. The organic phase was washed once with brine, dried over magnesium sulfate and solvent removed in vacuo. The crude residue was purified by silica gel (125 g) chromatography eluting with 30% acetone in hexanes. Yield: 6.4 g; MS (FAB) m/z: M+K=844.

EXAMPLE 2

Formula IIa: n=1; R$^1$=Et; R$^2$H; R$^3$OTBS; R$^4$H; R$^5$=H; R$^5$ and R$^7$ taken together=O; Y=O; R$^{11}$=OCH$_3$, where TBS is tert-butyldimethylsilyl The title compound was prepared from m-chloroperbenzoic acid and the title compound of Example 1(c) in the presence of cesium carbonate according to the procedure described in Example 1. MS (FAB) m/z: M+K=958.

EXAMPLE 3

Formula IIb; n=1; R$^1$Et; R$^2$=H; R$^3$=OH; R$^4$=H; R$^5$=H; R$^6$ and R$^7$ taken together=O; Z=OH; R$^{12}$=—CHO.

p-Toluenesulfonic acid mono hydrate (0.03 g) was added into a stirred solution of the title compound of Example 1 (6.4 g) in acetone (130 mL) and stirred at room temperature for 0.5 hour. Solvent was removed in vacuo. The solid residue was redissolved in acetone (130 mL) and stirred at room temperature for 2 hours. The process was repeated and stirring continued for an additional 3 hours. Solvent was removed in vacuo. The solid was purified by silica gel chromatography eluting with 70% acetone in hexanes. Yield: 6.4 g; MS (FAB) m/z: M+K=830.

EXAMPLE 4

Formula IIb: n=1;R$^1$=Et; R$^2$=H; R$^3$=OTBS; R$^4$=H; R$^5$=H; R6 and R$^7$ taken together=O; Z=OH; R$^{12}$=—CHO, The title compound was prepared from the title compound of Example 2 and p-toluenesulfonic acid in acetone according to the procedure described in Example 3. MS (FAB) m/z: M+K=944.

EXAMPLE 5

Formula IIb: n=1; R$^1$=Et; R$^2$=H; R$^3$=OTBS; R$^4$=H; R$^5$=H; R$^6$ and R$^7$ taken together=O; Z=OH; R$^{12}$=—CH$_2$OH.

L-selectride (13.6 mL, 1M in THF) was added dropwise over 30 minutes into a stirred solution of the title compound of Example 4 (7.6 g) in 100 mL of tetrahydrofuran (THF) at −78° C. After being stirred at −78° C. for 1 hour, 1N HCl (aq) was added into the reaction mixture to destroy excess reducing agent. After the addition of hydrochloric acid, the reaction mixture was allowed to stir at 0° C. for 15 minutes. The reaction mixture was partitioned between ether and 1N HCl (aq). The organic phase was washed once with brine, dried over magnesium sulfate and solvent removed in vacuo. The solid residue was purified by silica gel chromatography (90 g) eluting with 5% isopropanol in dichloromethane. Yield: 4.65 g; MS (FAB) m/z: M+K=946.

EXAMPLE 6

Formula IIb: n=1; R$^1$=Et; R$^2$=H; R$^3$=OTBS; R$^4$=H; R$^5$=H; R$^6$ and R$^7$ taken together=O; Z=NHBn; R$^{12}$=—CH$_2$OH. Bn: benzyl A solution of the title compound of Example 5 (0.6 g), 1-hydroxybenzotriazole (0.09 g), benzylamine (0.15 mL) and 1-(3-dimethylaminopropyl)-3-ethylcarbodiimide hydrochloride (0.19 g) in N,N-dimethylformamide (5 mL) was stirred at room temperature overnight. The reaction mixture was partitioned between 1:1 ether/ethyl acetate solution and water. The organic phase was washed once with brine, dried over magnesium sulfate and solvent removed in vacuo. The product was purified by silica gel chromatography (5 g) eluting with 40% acetone in hexanes. Yield: 0.56 g.

EXAMPLE 7

Formula IIb: n=1; R$^1$=Et; R$^2$=H; R$^3$=OH; R$^4$=H; R$^5$=H; R$^6$ and R$^1$ taken together=O; Z=NHBn; R$^{12}$=—CH$_2$OH.

A solution of HF (0.09 mL of 48% aq HF dissolved in 4.5 mL of acetonitrile) was added into a stirred solution of the title compound of Example 6 (0.45 g) in acetonitrile (0.5 mL) at 0° C. After being stirred at room temperature for 4 hours, the reaction was cooled to 0° C. and powdered sodium bicarbonate (1 g) was added and stirred for an additional hour. Solid was removed by filtration and solvent removed in vacuo. The solid was purified by silica gel chromatography (12 g) eluting with 35% acetone in hexanes. Yield: 0.24 g; MS (FAB) m/z: M+K=921. m.p. 150°–159° C.

$^{13}$CNMR: (CDCl$_3$-2 rotamers) 213.2, 212.6, 196.0, 192.6, 172.8, 169.4, 169.2, 165.7, 164.4, 139.6, 138.9, 138.5, 138.5, 133.6, 133.3, 131.8, 130.3, 128.6, 128.0, 127.9, 127.3, 123.5, 123.3, 98.7, 97.6, 80.5, 79.5, 77.4, 77.2, 77.0, 76.6, 75.4, 73.7, 72.9, 72.5, 69.3, 68.3, 65.8, 61.0, 60.9, 57.7, 57.2, 56.4, 56.2, 56.0, 55.2, 54.9, 53.0, 49.1, 48.5, 45.6, 44.0, 43.7, 43.6, 43.6, 40.2, 39.6, 39.4, 38.7, 38.7, 35.3, 34.5, 34.0, 33.9, 33.8, 33.7, 32.5, 31.5, 31.0, 27.4, 26.2, 26.1, 24.5, 24.4, 24.3, 24.2, 20.8, 19.9, 19.5, 16.1, 16.0, 15.6, 15.2, 14.2, 13.2, 11.7, 11.6, 10.0, 9.9 ppm.

EXAMPLE 8

Formula IIb: n=1; $R^1$=Et; $R^2$=H; $R^3$=OTBS; $R^4$=H; $R^5$=H; $R^6$ and $R^7$ taken together=O; Z=NHCH$_2$CH$_2$OH; $R^{12}$=—CH$_2$OH.

The title compound was prepared from the title compound of Example 5 (0.6 g), 1-hydroxybenzotriazole (0.09 g), aminoethanol (0.05 mL) and 1-(3-dimethylaminopropyl)-3-ethylcarbodiimide hydrochloride (0.19 g) in N,N-dimethylformamide (5 mL) according to the procedure described in Example 6.

Yield: 0.52 g.

EXAMPLE 9

Formula IIb; n=1; $R^1$=Et; $R^2$=H; $R^3$=OH; $R^4$=H; $R^5$=H; $R^6$ and $R^7$ taken =O; Z=NHCH$_2$CH$_2$OH; $R^{12}$=—CH$_2$OH.

The title compound was prepared from the title compound of Example 8 (0.49 g) and HF according to the procedures described in Example 7. Yield: 0.42 g; MS (FAB) m/z: M+K=875. m.p. 108°–115° C.

$^{13}$CMR: (CDCl$_3$-2 rotamers) 213.0, 212.9, 196.3, 193.1, 174.2, 169.5, 169.3, 165.6, 164.7, 138.9, 133.5, 133.2, 132.3, 130.9, 123.7, 123.4, 98.4,9 7.7,81.3,80.4,77.3,7 7.0, 76.8, 76.4, 75.4, 73.6, 72.9, 72.4, 69.0, 62.3, 61.0, 60.9, 57.6, 57.2, 56.5, 56.3, 56.1, 55.3, 54.8, 53.0, 49.3, 48.6, 46.3, 44.1, 42.5, 42.3, 40.8, 40.0, 39.5, 38.8, 38.7, 35.0, 34.7, 34.1, 33.9, 33.8, 33.8, 33.6, 32.6, 32.5, 31.4, 31.1, 30.9, 27.2, 26.1, 26.1, 26.0, 24.5, 24.3, 24.2, 20.7, 19.9, 19.6, 16.0, 16.0, 15.7, 15.6, 14.0, 13.1, 11.7, 11.6, 10.1, 9.9 ppm.

EXAMPLE 10

Formula IIa: n=1; $R^1$=Et; $R^2$=H; $R^3$=OTBS: $R^4$=H; $R^5$=H; $R^6$and $R^7$ taken together=O; Y=O; $R^{11}$=H, 2-Fluoro-l-methylpyridinium p-tolunesulfonate (Mukaiyama reagent, 0.374 g) was added into a stirred solution of the title compound of Example 5 (0.6 g) in dichloromethane (35 mL) containing triethylamine (0.185 mL) at room temperature. After being stirred at room temperature overnight, solvent was removed in vacuo. The product was purified by silica gel chromatography (20 g) eluting with 30% acetone in hexanes. Yield: 0.46 g; MS (FAB) m/z: M+K=928.

EXAMPLE 11

Formula IIa; n=1; $R^1$=Et; $R^2$=H; $R^3$=OH; $R^4$=H; $R^5$=H; $R^6$ and $R^7$ taken together=O; Y=O; $R^{11}$=H.

A solution of HF (0.045 mL of 48% aq HF in 2 mL of acetonitrile) was added into a stirred solution of the title compound of Example 10 (0.224 g) in acetonitrile (5 mL) at 0° C. After being stirred at room temperature for 2 hours, the reaction was cooled to 0° C. and powdered sodium bicarbonate (1 g) was added and stirred for an additional hour. Solid was filtered off and solvent removed in vacuo. Product was purified by silica gel chromatography (4 g) eluting with 30% acetone in hexanes. Yield: 0.13 g; MS (FAB) m/z: M+K=814. m.p. 115°–118° C.

$^{13}$CNMR: (CDCl$_3$-2 rotamers) 213.6, 213.5, 196.1, 192.4, 175.6, 169.0, 168.7, 165.8, 164.6, 139.7, 138.9, 133.5, 133.0, 128.3, 128.3, 123.3, 123.0, 98.7, 97.1, 77.6, 77.2, 77.0, 76.9, 76.7, 76.5, 75.2, 73.7, 73.6, 72.9, 72.2, 70.0, 68.9, 67.5, 57.7, 57.0, 56.6, 56.3, 56.1, 55.0, 54.7, 52.8, 48.6, 48.5, 43.9, 43.3, 42.9, 40.2, 39.6, 39.3, 38.8, 35.4, 35.4, 34.5, 33.7, 32.9, 32.9, 32.7, 32.5, 31.6, 28.9, 27.5, 26.4, 26.2, 25.9, 24.6, 24.5, 24.4, 24.1, 22.6, 21.2, 20.8, 20.5, 19.5, 16.2, 16.0, 15.9, 15.6, 14.3, 14.2, 14.1, 11.7, 9.8, 9.4 ppm.

EXAMPLE 12

Formula IIb: n=1; $R^1$=Et; $R^2$=H; $R^3$=OTBS; $R^4$=H; $R^5$=H; $R^6$ and $R^7$ taken together=O; Z=n-Propyl-NH—; $R^{12}$=—CH$_2$OH.

The title compound was prepared from the title compound of Example 5 (0.6 g), 1-hydroxybenzotriazole (0.09 g), n-propylamine(0.05 mL) and 1-(3-dimethylaminopropyl)-3-ethylcarbodiimide hydrochloride (0.19 g) in N,N-dimethylformamide (5 mL) according to the procedure described in Example 6.

Yield: 0.59 g.

EXAMPLE 13

Formula IIb; n=1; R1=Et; $R^2$=H; $R^3$=OH; $R^4$=H; $R^5$=H; $R^6$ and $R^7$ taken together=O; Z=n-Propyl-NH—; $R^{12}$=—CH$_2$OH.

The title compound was prepared from the title compound of Example 12 (0.39 g) and HF according to the procedures described in Example 7. Yield: 0.27 g; MS (FAB) m/z: M+K=873. m.p. 98°–102° C. $^{13}$CNMR: (CDCl$_3$-2 rotamers) 213.5, 212.7, 196.0, 192.4, 173.0, 173.0, 169.5, 169.3, 165.8, 164.5, 139.7, 138.9, 133.6, 133.3, 131.6, 130.1, 123.5, 123.2, 98.7, 9 7.6, 80.4, 79.3, 77.2, 77.0, 76.8, 76.4, 75.3, 73.6, 73.0, 72.4, 69.3, 68.5, 60.9, 60.9, 57.7, 57.1, 56.5, 56.3, 56.0, 55.2, 54.9, 53.0, 49.1, 48.5, 45.4, 44.0, 43.6, 41.4, 41.3, 40.1, 39.6, 39.4, 38.7, 38.6, 35.4, 34.6, 34.5, 33.8, 33.8, 32.5, 32.5, 31.6, 31.4, 31.0, 27.3, 26.2, 26.1, 26.0, 24.6, 24.4, 24.3, 24.2, 22.8, 20.8, 20.0, 19.4, 16.1, 16.0, 15.7, 15.6, 14.1, 13.4, 11.7, 11.6, 11.4, 10.0, 9.9 ppm.

EXAMPLE 14

Formula IIb: n=1; $R^1$=Et; $R^2$=H; $R^3$=OTBS; $R^4$=H; $R^5$=H; $R^6$ and $R^7$ taken together=O; Z=morpholine; $R^{12}$=—CH$_2$OH.

The title compound was prepared from the title compound of Example 5 (0.6 g), 1-hydroxybenzotriazole (0.09 g), morpholine (0.1 mL) and 1-(3-dimethylaminopropyl)-3-ethylcarbodiimide hydrochloride (0.19 g) in N,N-dimethylformamide (5 mL) according to the procedure described in Example 6.

Yield: 0.53 g; MS (FAB) m/z: M+K=1015

EXAMPLE 15

Formula IIb: n=1; $R^1$=Et; $R^2$=H; $R^3$=OH; $R^4$=H; $R^5$=H; $R^6$ and $R^7$ taken together=O; Z=morpholine; $R^{12}$=—CH$_2$OH.

The title compound was prepared from the title compound of Example 12 (0.46 g) and HF according to the procedures described in Example 7. Yield: 0.32 g; MS (FAB) m/z: M+K=901. m.p. 124°–130° C.

$^{13}$CNMR: (CDCl$_3$-2 rotamers) 213.6, 212.9, 196.1, 192.1, 171.7, 171.6, 169.3, 168.8, 165.8, 164.5, 139.6, 138.7, 133.6, 133.5, 130.9, 129.7, 123.2, 123.2, 98.6, 97.5, 79.7, 78.6, 77.4, 77.2, 77.0, 76.6, 76.4, 75.3, 73.6, 73.5, 72.9, 72.0, 69.5, 68.7, 66.8, 66.7, 66.7, 60.9, 60.9, 57.6, 57.0, 56.5, 56.3, 56.1, 55.1, 54.9, 52.9, 49.0, 48.6, 45.8, 44.7, 43.9, 43.4, 42.0, 40.0, 39.5, 39.4, 38.6, 35.5, 34.5, 34.2, 34.0, 33.5, 33.5, 32.6, 32.5, 31.6, 31.0, 30.5, 30.4, 30.2, 30.0, 27.3, 26.1, 25.8, 24.6, 24.5, 24.3, 20.9, 20.8, 20.1, 19.3, 16.1, 16.1, 15.7, 15.5, 14.6, 14.1, 13.7, 11.7, 11.6, 9.9, 9.9 ppm.

EXAMPLE 16

Formula IIb: n=1; $R^1$=Et; $R^2$=H; $R^3$=OTBS; $R^4$=H; $R^5$=H; $R^6$ and $R^7$ taken together=O; Z=OH; $R^{12}$=—$CH_2NH$—Bn.

The title compound is prepared from the title compound of Example 4, benzylamine and sodium cyanoborohydride in acetic acid at 0° C. The product is purified by reverse phase HPLC.

EXAMPLE 17

Formula IIb: n=1; $R^1$=Et; $R^2$=H; $R^3$=OH; $R^4$=H; $R^5$=H; $R^6$ and $R^7$ taken together=O; Z=OH; $R^{12}$=—$CH_2NH$—Bn.

The title compound is prepared from the title compound of Example 16 and hydrofluoric acid according to the procedure described in Example 7.

EXAMPLE 18

Formula IIb.: n=1; $R^1$=Et; $R^2$=H; $R^3$=OH; $R^4$=H; $R^5$=H; $R^6$ and $R^7$ taken together=O; Z=morpholine; $R^{12}$=—$CH_2NH$—Bn.

The title compound is prepared from the title compound of Example 17 and morpholine according to the procedure described in Example 6.

EXAMPLE 19

Formula IIb: n=1; $R^1$=Et; $R^2$=H; $R^3$=OH; $R^4$=H; $R^5$=H; $R^6$ and $R^2$ taken together =O; Z=OH; $R^{12}$=—$CH_2NH$—Me.

The title compound is prepared from the title compound of Example 3 and N-methylamine according to the procedure described in Example 16.

EXAMPLE 20

Formula IIb: n=1; $R^1$=Et; $R^2$=H; $R^3$=OH; $R^4$=H; $R^5$=H; $R^6$ and $R^7$ taken together=O; Z=morpholine; $R^{12}$=—$CH_2NH$—Me.

The title compound is prepared from the title compound of Example 19 and morpholine according to the procedure described in Example 6.

EXAMPLE 21

Formula IIc: n=1; $R^1$=Et; $R^2$=H; $R^3$=OTBS; $R^4$=H; $R^5$=H; $R^6$ and $R^7$ taken together=O; $R^{13}$=—CHO.

Isobutyl chloroformate (3.3 mL) was added dropwise into a stirred solution of the title compound of Example 4 (19.2 g), triethylamine (3.5 mL) and water (18 mL) in acetone (200 mL) at 0° C. over 5 minutes. After being stirred at 0° C. for 1 hour, a solution of sodium azide (2.75 g) in water (50 mL) was added to the reaction at 0° C. and stirred at this temperature for addtional 0. 5 hour. The reaction mixture was partitioned between ether (650 mL) and aqueous sodium bicarbonate (sat'd, 3×150 mL). The organic phase was washed once brine (150 mL), dried over magnesium sulfate and solvent removed in vacuo (safety shield!). The crude acyl azide (19.6 g) was purified by silica gel chromatography (250 g) eluting with 20% acetone in hexanes. Yield: 17.4 g. Portion of the acyl azide (2 g) in dry tetrahydrofuran (30 mL) was refluxed under nitrogen for 3 hours. Solvent was removed in vacuo and product purified by silica gel chromatography. Yield: 2 g; MS (FAB) m/z: M+K=941.

EXAMPLE 22

Formula IIc: n=1; $R^1$=Et; $R^2$=H; $R^3$=OH; $R^4$=H; $R^5$=H; $R^6$ and $R^7$ taken together=O; $R^{13}$=—CHO.

The title compound was prepared from the title compound of Example 3 (0.23 g), isobutyl chloroformate, triethylamine and sodium azide according to the procedure described in Example 21. Yield: 0.17 g; MS (FAB) m/z: M+K=827.

EXAMPLE 23

Formula IIb: n=1; $R^1$Et; $R^2$=H; $R^3$=OTBS; $R^4$=H; $R^5$=H; $R^6$ and $R^7$ taken together=O; Z=OH; $R^{12}$=—CH=$CH_2$, Lithium bis(trimethylsilyl)amide (2.3 mL, 1.0M in tetrahydrofuran) is added into a suspension of methyltriphenylphosphonium bromide (0.97 g) in dry toluene (7 mL) at 0° C. and stirred for 1 hour. A precooled solution of the product of Example 4 (0.7 g, in 14 mL of dry toluene) is added into the ylide over 7 minutes. After being stirred at 0° C. for 30 minutes, the reaction mixture is applied on a column of silica gel (50 g) in 40% acetone/hexanes and eluted with 40% acetone/hexanes to give the title compound.

EXAMPLE 24

Formula IIb: n=1; $R^1$=Et; $R^2$=H; $R^3$=OH; $R^4$=H; $R^5$=H; $R^6$ and $R^7$ taken together=O; Z=OH; $R^{12}$=—CH=$CH_2$, The title compound is prepared from the title compound of Example 23 and hydrofluoric acid according to the procedure described in Example 7.

EXAMPLE 25

Formula IIb: n=1; $R^1$=Et; $R^2$=H; $R^3$=OH; $R^4$=H; $R^5$=H; $R^6$ and $R^2$ taken together=O; Z=OH; $R^{12}$=—$CH_2CH_3$, The title compound is prepared by hydrogenation of the title compound of Example 24 in the presence of Pd/C in ethanol.

EXAMPLE 26

Formula IIb: n=1; $R^1$=Et; $R^2$=H; $R^3$=OH; $R^4$=H; $R^5$=H; $R^6$ and $R^2$ taken together=O; Z=OH; $R^{12}$=—CH(OH)$CH_2$(OH), N-methylmorpholine N-oxide (0.73 g) and osmium tetraoxide (1 mL, 4wt % in water) are added into a stirred solution of the product of Example 24 (0.7 g) in tetrahydrofuran (52 mL) and stirred at room temperature for 5 hours. Excess oxidizing agent is quenched with sodium bisulfite (0.9 g) and florisil. The reaction is then diluted with ethyl acetate and solid filtered off through celite. The filtrate is washed with 1N sodium bicarbonate, brine, dried over magnesium sulfate and solvent removed in vacuo. The product is purified by silica gel chromatography.

EXAMPLE 27

Formula IIb: n=1; $R^1$=Et; $R^2$=H; $R^3$=OH; $R^4$=H; $R^5$=H; $R^6$ and $R^7$ taken together=O; Z=OH; $R^{12}$=—CH=CHPh, The title compound is prepared from the title compound of Example 3 and benzyltriphenylphosphonium bromide according to the procedure described in Example 23.

EXAMPLE 28

Formula IIb: n=1; $R^1$=Et; $R^2$=H; $R^3$=OH; $R^4$=H; $R^5$=H; $R^6$ and $R^7$ taken together=O; Z=OH; $R^{12}$=—$CH_2CH_2Ph$, The title compound is prepared from the title compound of Example 27 and hydrogen in the presence of Pd/C according to the procedure described in Example 25.

EXAMPLE 29

Formula IIc: n=1; $R^1$=Et; $R^2$=H; $R^3$=OH; $R^4$=H; $R^5$=H; $R^6$ and $R^7$ taken together=O; $R^{13}$=—CH=$CH_2$, The title compound is prepared from the title compound of Example 24, isobutyl chloroformate and sodium azide according to the procedure described in Example 21.

EXAMPLE 30

Formula IIc: n=1; $R^1$=Et; $R^2$=H; $R^3$=OH; $R^4$=H; $R^5$=H; $R^6$ and $R^7$ taken together=O; $R^{13}$=—$CH_2CH_3$, The title compound is prepared from the title compound of Example 25, isobutyl chloroformate and sodium azide according to the procedure described in Example 21.

EXAMPLE 31

Formula IIb: n=$R^1$=Et; $R^2$=H; $R^3$=OH; $R^4$=H; $R^5$=H; $R^6$ and $R^7$ taken together=O; Z=OH; $R^{12}$=$CH_2OH$, The title compound is prepared from the title compound of Example 5 and hydrofluoric acid according to the procedure described in Example 7.

EXAMPLE 32

Formula IIc: n=1: $^1$=Et; $R^2$=H; $R^3$=OH; $R^4$=H; $R^5$=H; $R^6$ and $R^7$ taken together=O; $R^{13}$=—$CH_2OH$.

The title compound is prepared from the title compound of Example 31, isobutyl chloroformate and sodium azide according to the procedure described in Example 21.

EXAMPLE 33

Formula IId: n=1; $R^1$=Et; $R^2$=H; $R^3$=OH; $R^4$=H; $R^5$=H; $R^6$ and $R^7$ taken together=O; Z=morpholino; $R^{13}$=—$CH_2CH_3$, Morpholine (0.6 mL) is added into a stirred solution of the title compound of Example 30 (2.5 g) in dry tetrahydrofuran (25 mL) at room temperature for 1 hour. Solvent is removed in vacuo and product purified by silica gel chromatography.

EXAMPLE 34

Formula IId: n=1; $R^1$=Et; $R^2$=H; $R^3$=OH; $R^4$=H; $R^5$=H; $R^6$ and $R^7$ taken together=O; Z=morpholino; $R^{13}$=—CH=$CH_2$, The title compound is prepared from the title compound of Example 29 and morpholine in dry tetrahydrofuran according to the procedure described in Example 33.

EXAMPLE 35

Formula IId; n=1; $R^1$=Et; $R^2$32 H; $R^3$=OH; $R^4$=H; $R^5$=H; $R^6$ and $R^7$ taken together=O; Z=BnNH—; $R^{13}$=—CH=$CH_2$, The title compound is prepared from the title compound of Example 29 and benzylamine in dry tetrahydrofuran according to the procedure described in Example 33.

EXAMPLE 36a

Formula IIe: n=1; $R^1$=Et; $R^2$=H; $R^3$=OTBS; $R^4$=H; $R^5$=H; $R^6$ and $R^2$ taken together=O, L-selectride (0.76 mL, 1M solution in THF, Aldrich) was added dropwise into a stirred solution of the title compound of Example 21 (0.55 g) in dry tetrahydrofuran (5 mL) at –78° C. in ten minutes. After being stirred at –78° C. for 15 minutes, the reaction was partitioned between ether and 1 N hydrochloric acid. The organic phase was washed once with brine, dried over magnesium sulfate and solvent removed in vacuo. The product was purified by silica gel chromatography (25 g) eluting with 30% acetone/hexanes. Yield: 0.26 g; MS (FAB) m/z: M+K=943.

EXAMPLE 36b

Formula IId: n=1; $R^1$=Et; $R^2$=H; $R^3$=OTBS; $R^4$=H; $R^5$=H; $R^6$ and $R^7$ taken together=O; Z=H; $R^{13}$=—$CH_2OH$, The title compound was purified from the crude products of Example 36a. Yield: 0.04 g; MS (FAB) m/z: M+K=945.

EXAMPLE 36c

Formula IId; n=1; $R^1$=Et; $R^2$=H; $R^3$=OH; $R^4$=H; $R^5$=H; $R^6$ and $R^7$ taken together=O; Z=H; $R^{13}$=—$CH_2OH$, The title compound is prepared from the title compound of Example 36b and hydrofluoric acid according to the procedure described in Example 7.

EXAMPLE 37

Formula IIe: n=1: $^1$=Et; $R^2$=H; $R^3$=OH; $R^4$=H; $R^5$=H; $R^6$ and $R^1$ taken together=O, The title compound was prepared from the title compound of Example 36a and hydrofluoric acid according to the procedure described in Example 7. MS (FAB) m/z: M+K= 829.

EXAMPLE 38

Formula IIf: n=1; $R^1$Et; $R^2$=H; $R^3$=OTBS; $R^4$=H; $R^5$=H; $R^6$ and $R^7$ taken together=O; A=S; $R^{14}$=H, The title compound of Example 4 (0.7 g) was dissolved in a solution of ethanol (freshly distilled from sodium, 5 mL) containing aminothioethanol hydrogen chloride (0.2 g) under nitrogen at room temperature. Diisopropylethylamine (0.14 mL) was added to the reaction mixture followed by powdered magnesium sulfate. After being stirred at room temperature for 1.5 hour, the solids were filtered off and solvent removed in vacuo. The intermediate was purified by silica gel chromatography. Yield: 0.56 g. The intermediate (0.56 g) was dissolved in dry THF (5 mL) under nitrogen at room temperature. Diisopropyl carbodiimide (0.18 mL), hydroxybenzotriazole (0.078 g) and N-methylmorpholine (0.096 mL) was added to the THF solution and stirred at room temperature overnight. Solvent was removed in vacuo and the product was purified by silica gel chromatography (13 g) eluting with 30% acetone in hexanes. Yield: 0.55 g.

EXAMPLE 39

Formula IIf: n=1; $R^1$=Et; $R^2$=H; $R^3$=OH; $R^4$=H; $R^5$=H; $R^6$ and $R^7$ taken together=A=S; $R^{14}$=H, The title compound was prepared by reacting the title compound of Example 38 (0.55 g) and hydrofluoric acid according to the procedure described in Example 7. Yield: 0.23 g; MS (FAB) m/z: M+K=871. m.p. 117°–125° C.

$^{13}$CNMR: (CDCl$_3$-mixture of isomers each w/2 rotamers) 213.6, 213.5, 213.3, 213.2, 196.1, 196.0, 193.1, 192.4, 172.5, 172.4, 172.2, 169.0, 169.0, 168.9, 168.6, 165.8, 165.6, 164.7, 164.5, 139.7, 139.6, 138.9, 138.8, 134.6, 134.2, 133.1,132.5, 128.6, 128.6, 126.4, 126.0, 123.4, 123.2, 123.1, 123.0, 98.7, 98.7, 97.2, 97.0, 78.2, 78.0, 77.5, 77.3, 77.0, 76.9, 76.8, 76.5, 76.3, 75.3, 75.2, 73.7, 73.6, 73.6, 72.9, 72.6, 72.1, 70.0, 69.8, 69.1, 68.8, 61.2, 61.2, 58.2, 57.7, 57.5, 57.1, 57.0, 56.6, 56.6, 56.3, 56.1, 55.9, 55.0, 54.8, 54.7, 53.0, 52.7, 50.3, 50.2, 48.8, 48.6, 48.5, 48.5, 44.1, 43.8, 43.7, 43.7, 43.6, 43.3, 43.3, 42.8, 42.5, 42.4, 40.3, 40.1, 40.0, 40.0, 39.7, 39.6, 39.6, 39.4, 39.3, 36.6, 35.5, 35.1, 34.6, 34.5, 34.5, 34.0, 33.6, 33.2, 33.1, 32.9, 32.8, 32.7, 32.6, 32.6, 32.5, 31.6, 29.2, 29.2, 27.6, 27.6, 27.3, 26.4, 26.3, 26.2, 26.1, 26.0, 24.6, 24.6, 24.5, 24.4, 24.3, 24.2, 24.2, 22.6, 21.2, 21.1, 20.9, 20.8, 20.5, 20.4, 19.6, 19.4, 16.2, 16.0, 16.0, 15.9, 15.8, 15.7, 15.6, 14.4, 14.2, 14.1, 11.7, 10.1, 9.8, 9.4 ppm.

EXAMPLE 40

Formula IIf: n=1; R$^1$=Et; R$^2$=H; R$^3$=OH; R$^4$=H; R$^5$=H; R$^6$ and R$^7$ taken together=O; A=O; R$^{14}$=H.

The title compound is prepared from the title compound of Example 3 and aminoethanol according to the procedure described in Example 38.

EXAMPLE 41

Formula IIf: n=1d; R$^1$=Et; R$^2$=H; R$^3$=OH; R$^4$=H; R$^5$=H; R$^6$ and R$^7$ taken together=O; A=S; R$^{14}$s taken together with the carbons they attached to=—Ph—.

The title compound is prepared from the title compound of Example 3 and 2-aminothiophenol according to the procedure described in Example 38.

EXAMPLE 42

Formula IIf: n=1; R$^1$=Et; R$^2$=H; R$^3$=OH; R$^4$=H; R$^5$=H; R$^6$ and R$^7$ taken together=O; A=NH; R$^{14}$s taken together with the carbons they attached to=—Ph—.

The title compound is prepared from the title compound of Example 3 and o-phenylenediamine according to the procedure described in Example 38.

EXAMPLE 43

Formula IIg: n=1; R$^1$=Et; R$^2$=H; R$^3$=OTBS; R$^4$=H; R$^5$=H; R$^6$ and R$^7$ taken together=O; R$^{15}$=OH Diphenylphosphoryl azide (0.8 mL) was added into a solution of the title compound of Example 4 (0.98 g) and triethylamnine (0.26 mL) in dry tetrahydrofuran (3.5 mL) at room temperature. The reaction was stirred at 70° C. for 1 hour. After being cooled down to room temperature, the reaction mixture was poured to silica gel (25 g) and eluted with 10%. acetone/hexanes followed by 30% acetone/hexanes. Yield: 0.34 g; MS (FAB) m/z: M+K=984.

EXAMPLE 44

Formula IIg: n=1; R$^1$=Et; R$^2$=H; R$^3$=OH; R$^4$=H; R$^5$=H; R$^6$ and R$^7$ taken together=O; R$^{15}$=OH.

The title compound was prepared from the title compound of Example 3 and diphenylphosphoryl azide according to the procedure described in Example 43. MS (FAB) m/z: M+K=870. m.p. 135°–143° C.

$^{13}$CNMR:(CDCl$_3$-2 rotamers) 213.2, 196.1, 192.9, 169.0, 168.8, 165.9, 164.8, 154.3, 154.0, 139.6, 138.8, 134.1, 134.0, 133.6, 127.8, 124.3, 123.5, 123.2, 112.8, 112.7, 111.5, 111.4, 98.8, 97.2, 78.0, 78.0, 77.5, 77.2, 77.0, 76.8, 75.4, 73.9, 73.9, 73.1, 72.5, 70.0, 69.0, 65.8, 57.5, 57.0, 56.7, 56.2, 55.9, 55.1, 54.8, 52.9, 48.8, 48.6, 43.9, 43.7, 43.7, 43.4, 42.2, 42.1, 40.9, 40.6, 40.5, 40.0, 39.9, 39.3, 35.5, 34.6, 33.8, 33.2, 32.8, 32.7, 30.9, 28.2, 27.9, 27.5, 26.5, 26.4, 26.2, 24.6, 24.6, 24.4, 24.3, 21.2, 20.8, 20.5, 19.6, 16.2, 15.9, 15.8, 15.8, 15.2, 14.3, 14.2, 11.6, 9.9, 9.6 ppm.

EXAMPLE 45

Formula IIh: n=1; R$^1$=Et; R$^2$=H; R$^3$=OH; R$^4$=H; R$^5$=H; R$^6$ and R$^7$ taken together=O A solution of hydrofluoric acid (0.06 mL in 1 mL acetonitrile) was added into a stirred solution of the title compound of Example 22 (0.16 g) in acetonitrile (1.5 mL) at 0° C. After being stirred at 0° C. for 2.5 hours, powdered sodium bicarbonate (0.5 g) was added and stirred for another haft hour. The reaction mixture was purified by C-18 reverse phase HPLC eluting with aqueous acetonitrile containing 0.2% trifluoroacetic acid. Yield after lyophilization: 0.103 g; MS (FAB) m/z: M+K=783.

EXAMPLE 46

Formula IIi: n=1; R$^1$=Et; R$^2$=H; R$^3$=OH; R$^4$=H; R$^5$=H; R$^6$ and R$^7$ taken together=O A suspension of 10% Pd/C in a solution of the title compound of Example 45 in tetrahydrofuran is stirred under an atmosphere of oxygen at room temperature for 10 days. Solids are filtered off and solvent removed in vacuo. The product is purified by silica gel chromatography.

EXAMPLE 47

Formula IIj: n=1; R$^1$=Et; R$^2$=H; R$^3$=OH; R$^4$=H; R$^5$=H; R$^6$ and R$^7$ taken together=O; R$^{16}$=H.

A solution of the title compound of Example 45 (32 mg) in methanol was hydrogenated under 1 atm of hydrogen in the presence of 5% Rh/Al$_2$O$_3$ for 2 hours. The product was purified by reverse phase HPLC. MS (FAB) m/z: M+K=785.

EXAMPLE 48

Formula IIj: n=1; R$^1$=Et; R$^2$=H; R$^3$=OTBS; R$^4$=H; R$^5$=H; R$^6$ and R$^7$ taken together=O; R$^{16}$=H.

The title compound is prepared from the title compound of Example 47 and hydrogen according to the procedure described in Example 47.

EXAMPLE 49

Formula IIj: n=1; $^1$=Et; R$^2$=H; R$^3$=OH; R$^4$=H; R$^5$=H; R$^6$ and R$^7$ taken together=O; R$^{16}$=—CH$_2$Ph, Benzyl bromide is added into a stirred solution of the title compound of Example 47 and triethylamine in N,N-dimethylformamide. The product is purified by reverse phase HPLC.

EXAMPLE 50

Formula IIj: n=1; R$^1$=Et; R$^2$=H; R$^3$=OH; R$^4$=H; R$^5$=H; R$^6$ and R$^7$ taken together=O; R$^{16}$=methyl.

The title compound is prepared from the title compound of Example 47, methyl iodide and triethylamine according to the procedure described in Example 49.

EXAMPLE 51

Formula IIj; n=1; $R^1$=Et; $R^2$=H; $R^3$=OH; $R^4$H; $R^5$=H; $R^6$ and $R^7$ taken together=O; $R^{16}$=—$CH_2CH_2OH$.

The title compound is prepared from the title compound of Example 47, ethylene oxide and triethylamine according to the procedure described in Example 49.

EXAMPLE 52

Formula IIk: n=1; $R^1$=Et; $R^2$=H; $R^3$=OH; $R^4$=H; $R^5$=H; $R^6$ and $R^7$ taken together=O; Z=PhNH—; $R^{15}$=H, The title compound is prepared from the title compound of Example 47, phenyl isocyanate and triethylamnine according to the procedure described in Example 49.

EXAMPLE 53

Formula IIk: n=1; $^1$=Et; $R^2$=H; $R^3$=OTBS; $R^4$=H; $R^5$=H; $R^6$ and $R^7$ taken together=O; Z=morpholin-1-yl; $R^{15}$=OH.

Morpholine (0.6 mL, neat) was added into a stirred solution of the title compound of Example 21 (2.5 g) in tetrahydrofuran (25 mL) at room temperature. After being stirred at room temperature for 0.5 hour, the solvent was removed in vacuo and the product purified by silica gel chromatography (150 g) eluting with 40% acetone/hexanes. Yield: 1.7 g; MS (FAB) m/z: M+K=1028.

EXAMPLE 54

Formula IIm: n=1; $R^1$=Et; $R^2$=H; $R^3$=OTBS; $R^4$=H; $R^5$=H; $R^6$ and $R^7$ taken together=O; Z=morpholin-1-yl, Methanesulfonyl chloride (0.31 mL) was added into a stirred solution of the title compound of Example 53 (1.58 g) in dry tetrahydrofuran (16 mL) at 0° C. Triethylamine (0.9 mL) was added dropwise to the reaction solution at 0° C. over 10 minutes. After being stirred for 1 hour, the reaction was partitioned between water and ether, the organic phase washed once with brine, dried over magnesium sulfate and solvent removed in vacuo. The product was purified by silica gel chromatography (50 g) eluting with 20% acetone/hexanes. Yield: 0.953 g; MS (FAB) m/z: M+K=1010.

EXAMPLE 55

Formula IIx: n=1; $R^1$=Et; $R^2$=H; $R^3$=OTBS; $R^4$=H; $R^5$=H; $R^6$ and $R^7$ taken together=O;Z=morpholin-1-yl; $R^{15}$=H.

A solution of the title compound of Example 54 (0.825 g) in methanol was hydrogenated over 1 atm of hydrogen in the presence of Rh/$Al_2O_3$ for 3 hours. The solids were filtered off and solvent removed in vacuo. The product was purified by silica gel chromatography (25 g) during with 25 % ethyl acetate/methylene chloride. Yield: 0.6 19 g.

EXAMPLE 56

Formula IIk; n=1; $R^1$=Et; $R^2$=H; $R^3$=OH; $R^4$=H; $R^5$=H; $R^6$ and $R^7$ taken together=O; Z=morpholin-1yl; $R^{15}$=H.

The title compound of Example 56 was prepared from the product of Example 55 (0.32 g) and hydrofluoric acid according to the procedure described in Example 7. The product was purified by C-18 reverse HPLC during with aqueous acetonitrile containing 0.1% trifluoroacetic acid. Yield: 0.235 g; MS (FAB) m/z: M+K=898.

EXAMPLE 57

Formula IIk: n=1; $R^1$=Et; $R^2$=H; $R^3$=OH; $R^4$=H; $R^5$=H; $R^6$ and $R^7$ taken together=O; Z=Ph; $R^{15}$=H, The title compound is prepared from the title compound of Example 48 and benzoyl chloride in the presence of N-methylmorpholine.

EXAMPLE 58

Formula IIn: n=1; $R^1$Et; $R^2$=H; $R^3$=OH; $R^4$=H; $R^5$=H; $R^6$ and $R^7$ taken together=O, Aqueous phosphoric acid (1 wt %, 2 mL) was added into a stirred solution of the title compound of Example 21 (1.05 g) in dioxane (12 mL) and stirred at room temperature for 1.5 hour. The reaction mixture was partitioned between ether and sodium bicarbonate. The organic phase was dried over magnesium sulfate and solvent removed in vacuo. The product was purified by silica gel chromatography (25 g) eluting with 18% acetone in hexanes. Yield: 0.35 g; MS (FAB) m/z: M+K=941.

EXAMPLE 59

Formula IIm: n=1; $R^1$=Et; $R^2$=H; $R^3$=OH; $R^4$=H; $R^5$=H; $R^6$ and $R^2$ taken together=O; Z=morpholino, The title compound is prepared from the title compound of Example 54 and hydrofluoric acid according to the procedure described in Example 7.

EXAMPLE 60

Formula IId': n=1; $R^1$=Et; $R^2$=H; $R^3$=OH; $R^4$=H; $R^5$=H; $R^6$ and $R^7$ taken together=O; $R^{13}$=—CH=$CH_2$, The title compound is prepared from the title compound of Example 29 and hydrofluoric acid according to the procedure described in Example 7. The product is purified by reverse phase HPLC.

EXAMPLE 61

In Vitro Assay of Biological Activity

The immunosuppressant activity of the compounds of the present invention was determined using the human mixed lymphocyte reaction (MLR) assay described by T. Kino et al. in *Transplantation Proceedings*, XIX(5):36–39, Suppl. 6 (1987). The results of the assay, shown below in Table 1, demonstrate that the compounds tested are effective immunomodulators at low concentration.

TABLE 1

| Example # | $LC_{50}$ (M) |
| --- | --- |
| 7 | $23 \times 10^{-9}$ |
| 9 | $65 \times 10^{-9}$ |
| 11 | $1.1 \times 10^{-9}$ |
| 13 | $388 \times 10^{-9}$ |
| 15 | 25% at $1 \times 10^{-6}$ |
| 37 | $0.57 \times 10^{-9}$ |
| 39 | $37 \times 10^{-9}$ |
| 44 | $75 \times 10^{-9}$ |
| 56 | $2.6 \times 10^{-9}$ |

The compounds of the invention possess immunomodulatory activity in mammals (especially humans). The potent immunomodulatory activity which compounds of the instant invention demonstrate, in common in vitro biological assays, indicate that these compounds possess immunosuppressive, antimicrobial, antifungal, antiviral, antiinflammatory, and antiproliferative activity, and possess the ability to reverse chemotherapeutic drug resistance. While the compounds of the invention would be useful when used alone, combination therapy with other immunosuppressants, such as, FK506, rapamycin, cyclosporin A, picibanil, mycophenolic acid, azathioprine, prednisolone, cyclophosphamide, brequinar and leflunomide, would also be expected to be beneficial.

As immunosuppressants, the compounds of the present invention are useful when administered for the prevention of immune-mediated tissue or organ graft rejection. Examples of transplanted tissues and organs which suffer from these effects are heart, kidney, liver, lung, small-bowel, and the like. The regulation of the immune response by the compounds of the invention would also find utility in the treatment of autoimmune diseases, such as rheumatoid arthritis, Hashimoto's thyroiditis, multiple sclerosis, myasthenia gravis, type I diabetes, uveitis, allergic encephalomyelitis, glomerulonephritis, and the like.

Further uses include the treatment and prophylaxis of inflammatory and hyperproliferative skin diseases and cutaneous manifestations of immunologically-mediated illnesses, such as psoriasis, atopical dermatitis, and Epidermolysis bullosa. Further instances where a compound of the invention would be useful include various eye diseases (autoimmune and otherwise) such as ocular pemphigus, Scleritis, and Graves' opthalmopathy, etc.

Other treatable conditions would include but are not limited to intestinal inflammations/allergies such as Crohn's disease and ulcerative colitis; renal diseases such as interstitial nephritis; skin diseases such as dermatomyositis; hematic diseases such as aplastic anemia, idiopathic thrombocytopenic purpura, and autoimmune hemolytic anemia; circulatory diseases such as myocardosis; collagen diseases such as Wegener's granuloma; nephrotic syndrome such as glomerulonephritis; Pyoderma; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia)

When used in the above or other treatments, a therapeutically-effective amount of one of the compounds of the present invention, meaning a sufficient amount of the compound to treat a particular disorder, at a reasonable benefit/risk ratio, may be employed in pure form or, where such forms exist, in pharmaceutically acceptable salt, ester or prodrug form. Alternatively, the compound may be administered as pharmaceutical compositions containing the compound of interest in combination with one or more pharmaceutically-acceptable excipients. It will be understood, however, that the total daily usage of the compounds and compositions of the present invention will be decided by the attending physician within the scope of sound medical judgment.

The specific therapeutically-effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.001 to about 10 mg/kg of patients body mass/day. For purposes of oral administration, more preferable doses may be in the range of from about 0.005 to about 3 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of 10 the invention and a pharmaceutically-acceptable carder or excipient, meaning a non-toxic solid, semi-solid or liquid filler, diluent, encapsulating material or formulation auxiliary of any type, which may be administered orally, rectally, parenterally, intracisternally, intravaginally, intraperitoneally, topically (as by powders, ointments, drops or transdermal patch), bucally, or as an oral or nasal spray. The term "parenteral" as used herein refers to modes of administration which include rotravenous, intramuscular, intraperitoneal, intrastemal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carder, such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, cemain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions may contain, in addition to the active compounds, suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a lager-sized pharmaceutically-acceptable inert carder comprising particles having a size, for example, of up to 100 micrometers in diameter. Suitable inert carders include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autommune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically-acceptable ophthalmic vehicle may, for example, be an ointment, vegetable oil or an encapsulating material.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologicallyacceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula:

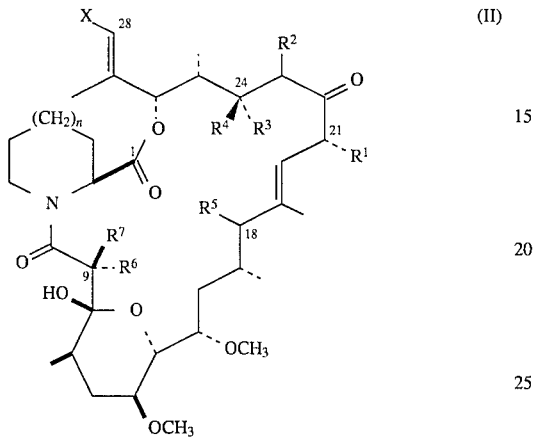

or a pharmaceutically acceptable salt, ester amide or prodrug thereof wherein the ester is selected from C1-to-C6 alkyl esters, C5-to-C7 cycloalkyl esters, arylalkyl esters and esters derived alcohol groups in the parent drug by reaction with C1-to-C6 carboxylic acids, C1-to-C6 dicarboxylic acids or aryl-carboxylic acids and wherein the amide result from reaction of a carboxylic acid moiety in the compound of formula II with $NH_3$, $NH_2(C1–C6\text{-alkyl})$, $NH(C1–C6\text{-alkyl})_2$ or a 5- or 6-membered heterocycle containing one nitrogen atom and wherein the prodrug is selected from the group consisting of (a) acyloxymethyl esters of carboxylic acids, (b) (5-methyl-2-oxo-1,3-dioxolen-4-yl)methyl esters of carboxylic acids, (c) esters derived from alcohol groups in the parent drug by reaction with succinic acid, phosphoric acid, dialkylaminoacetic acid or an amino acid (d) N-Mannich bases of amides or amines, (e) N-hydroxymethyl derivatives of amides, (f) N-acyloxyalkyl derivatives of amides or heterocyclic amines, (g) oxazolidinones derived from ketone groups in the parent drug by reaction with 2-aminoethanol; N-methyl-2-aminoethanol, N-(2-hydroxyethyl)-2-aminoethanol, 2-aminopropanol, 2-amino-2-methylpropanol, 2-amino-2-hydroxymethylpropanol, 3-amino-2-hydroxypropane, 2-amino-1-phenylethanol, 3-aminopropanol or N-methyl-2-amino-1-phenylpropanol and (h) enol esters derived from ketone groups in the parent drug, wherein n is zero or one;

$R^1$ is selected from the group consisting of methyl, ethyl, propyl, cyclopropylmethyl, 2-oxopropyl, 2-ethanal, 2-hydroxyethyl and allyl;

$R^2$ is hydrogen or $R^2$ taken together with $R^3$ forms a C-22/C-23 bond;

$R^3$ is selected from the group consisting of hydrogen, hydroxy and protected hydroxy; or $R^2$ taken together with $R^3$ forms a C-22/C-23 bond; or $R^3$ taken together with $R^4$ is oxo;

$R^4$ is hydrogen or $R^4$ taken together with $R^3$ is oxo;

$R^5$ is selected from hydrogen, hydroxy, protected hydroxy and fluoro;

$R^6$ and $R^7$ are independently selected from hydrogen, hydroxy and protected hydroxy, with the proviso that at least one of $R^6$ and $R^7$ is hydrogen; or $R^6$ and $R^7$ taken together are oxo;

X is a substituent selected from the group of radicals having the subformulae:

 (IIa)

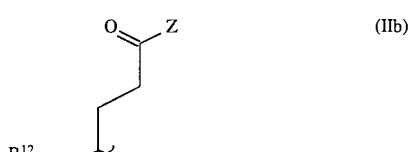 (IIb)

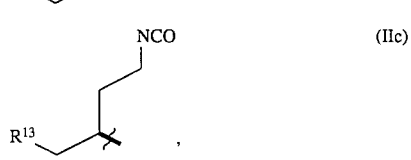 (IIc)

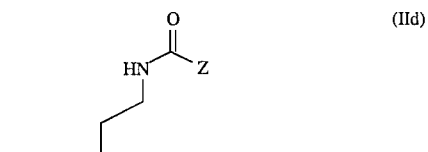 (IId)

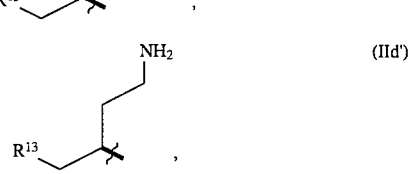 (IId')

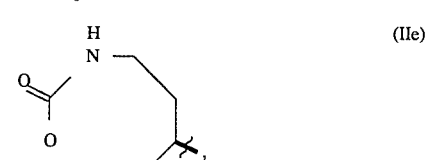 (IIe)

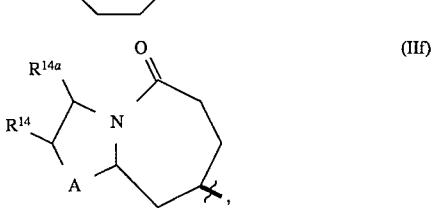 (IIf)

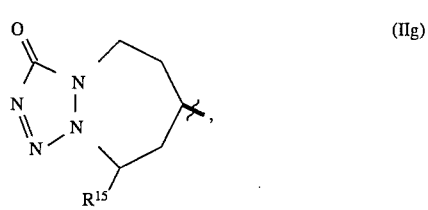 (IIg)

 (IIh)

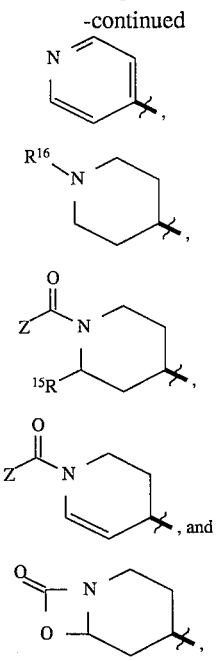

(IIi), (IIj), (IIk), (IIm), (IIn)

wherein
A is —O— or —S—;
Y is —O— or —NR²¹— wherein R²¹ is selected from the group consisting of:
(1) hydrogen,
(2) —(C1–C10-alkyl) optionally substituted with hydroxy, amino, aryl or heterocyclic,
(3) aryl and
(4) heterocyclic;

Z is selected from the group consisting of hydrogen, hydroxy, —(C1–C10-alkyl), aryl, heterocyclic, —(C1–C10-alkoxy) and —NR²³R²⁴, wherein R²³ and R²⁴ are independently selected from:
(1) hydrogen,
(2) aryl,
(3) heterocyclic and
(4) —(C1–C10-alkyl) optionally substituted with hydroxy, amino, aryl or heterocyclic,
or, alternatively, —NR²³R²⁴ represents a 3- to 7-membered heterocyclic ting, with the proviso that in subformulae (IId), (IIk) and (IIm) Z is other than hydroxy;

R¹¹ is hydrogen, hydroxy or methoxy;
R¹² is selected from the group consisting of:
(1) —CHO,
(2) —(C1–C10-alkyl) optionally substituted with one, two or three substituents independently selected from the group consisting of hydroxy, amino, aryl and heterocyclic,
(3) —(C2–C10-alkenyl) optionally substituted with aryl or heterocyclic,
(4) —CH₂-NR²¹R²² where R²¹ is independently defined as above and R²² is hydrogen or acyl;

R¹³ is selected from the group consisting of —CHO, hydroxy, protected hydroxy, —(C2–C10-alkenyl) optionally substituted with aryl and —(C1–C10-alkyl) optionally substituted with aryl, with the proviso that in subformula (IId') R¹³ is other than —CHO;

R¹⁴ and R¹⁴ᵃ are independently selected from hydrogen, aryl, heterocyclic and —(C1–C10-alkyl) or, taken together with the carbon atoms to which they are attached, R¹⁴ and R¹⁴ᵃ form an aryl group or a heterocyclic group;

R¹⁵ is hydrogen or hydroxy; and
R¹⁶ is selected from the group consisting of
(1) hydrogen,
(2) —(C1–C10-alkyl) optionally substituted with hydroxy, amino, aryl or heterocyclic,
(3) aryl,
(4) heterocyclic and
(5) —C(=NH)—NH₂;

wherein at each occurrence the hydroxy protecting group is independently selected from methoxymethyl, methylthiomethyl, 2-methoxyethoxymethyl, benzyloxymethyl, 2-(trimethylsilyl)ethoxymethyl, t-butyl, benzyl, triphenylmethyl, tetrahydropyranyl 2,2,2-trichloroethyl, tris(C1-to-C10-alkyl)silyl, (C1-to-C10)loweralkyldiarylsilyl, triphenyimethyldimethylsilyl, triarylsilyl, triarylalkylsilyl, —C(O)H, —C(O)(C1-to-C10-alkyl), —C(O)-aryl, alkoxycarbonyl, —S(O)₂-(C1-to-C10 alkyl), and —S(O)₂-(aryl);

wherein at each occurrence the aryl group is independently selected from phenyl, 1-naphthyl, 2-naphthyl, fluorenyl, (1,2)-dihydronaphthyl, (1,2,3,4,)-tetrahydronaphthyl and indenyl and wherein each aryl group is unsubstituted or substituted with one, two or three substituents independently selected from the group consisting of —(C1–C10-alkyl), —(C2–C10-alkenyl), halogen, —(CH₂)ₘN(C1–C6-alkyl)₂, wherein m is zero to six, —CN, —CHO, mono-, di-, tri-, or perhalogenated —(C1–C6-alkyl), —S(O)ₚ(C1–C6-alkyl), wherein p is 0, 1 or 2, —C(O)N(C1–C6-alkyl), —(CH₂)ₘO(C1–C6-alkyl), where m is as defined above, (CH₂)_qOC(O)(C1–C6-alkyl), wherein q is zero to six, (CH₂)ᵣC(O)O(C1–C6-alkyl), wherein r is zero to six, —NO₂, —N₃, —S(O)₂N(C1–C6-alkyl)₂, —(C2-to-C10-alkynyl), —C≡C—Si(CH₃)₃, guanidino, hydroxy, —COOH, —(C1–C6-alkoxy), —OC(O)(C1–C6-alkyl), unsubstituted aryl and unsubstituted Het;

wherein at each occurrence the Het group or heterocyclic group is independently selected from the group consisting of indolyl, quinolyl, isoquinolyl, tetrahydroquinolyl, benzofuryl, dihydrobenxofuryl, benzothienyl, azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolidinyl. morpholinyl, thiomorpholinyl, thiazolyl, isothiazolidinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrimidyl, cytosinyl, thiosytosinyl, xanthenyl, xanthonyl, uricyl, thyminyl, and compounds of the formula

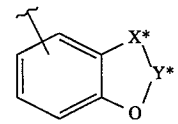

where X* is —CH₂— or —O— and Y* is —C(O)— or [C(R")₂—]y where R" is hydrogen or C1–C4-alkyl and y is 1, 2 or 3 and wherein each heterocyclic group is unsubstituted, monosubstituted or disubstituted with substituents independently selected from —(C1-to-C10 alkyl), —(C2-to-C10-alkenyl), halogen, amino, —(CH₂)_fN(C1–C6-alkyl)₂, wherein f is 0 to 6, —CN, —CHO, mono-, di-, tri-, or perhalogenated —(C1–C6- alkyl), —S(O)$_g$(C1–C6-alkyl) wherein g is 0, 1 or 2, —C(O)N(C1–C6-alkyl), —(CH$_2$)$_h$N(C1–C6-alkyl), wherein h is 0 to 6, —(CH$_2$)$_i$OC(O)(C1–C6-alkyl) wherein i is 0 to 6, —(CH$_2$)$_j$C(O)O(C1–C6-alkyl), wherein j is 0 to 6, —NO$_2$, —N$_3$, —S(O)$_2$N(C1–C6-alkyl)$_2$, —(C2–C10-alkynyl), —C≡C—Si(CH$_3$)$_3$, guanidino, hydroxy, —COOH, —(C1–C6-alkoxy), —OC(O)(C1–C6-alkyl), oxo (=O), unsubstituted aryl and unsubstituted Het; and wherein at each occurrence the acyl group is independently selected from —C(O)R$^{30}$ wherein R$^{30}$ is aryl, (C1–C10-alkyl), (C2–C10-alkenyl) or heterocyclic.

2. A compound according to claim 1 of the formula

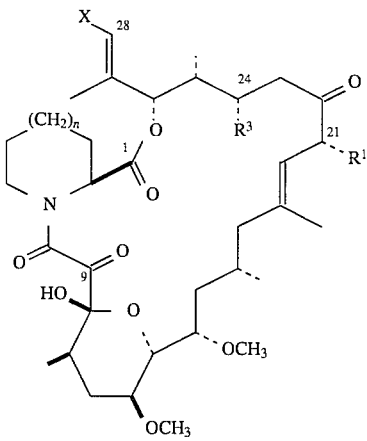

(III)

wherein n is one, R$^1$ and R$^3$ are as defined therein and X is a substituent selected from the group of radicals having the subformulae:

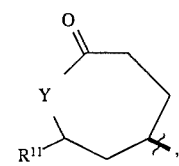

(IIa)

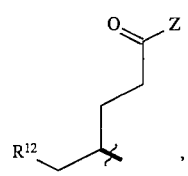

(IIb)

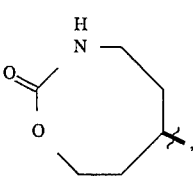

(IIe)

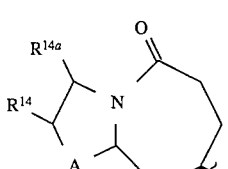

(IIf)

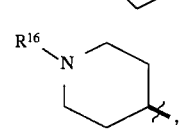

(IIj)

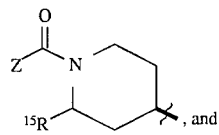

(IIk)

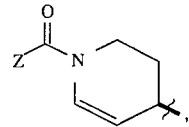

(IIm)

wherein A, Y, Z, R$^{12}$, R$^{14}$, R$^{14a}$ and R$^{16}$ are as defined therein and R$^{11}$ and R$^{15}$ are each hydrogen.

3. A compound according to claim 2 wherein X is a substituent selected from the group of radicals having the subformulae:

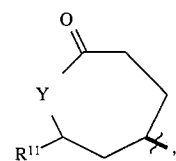

(IIa)

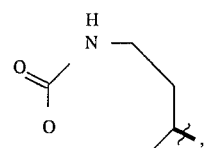

(IIe)

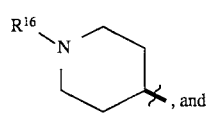

(IIj)

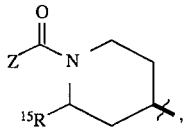

(IIk)

wherein Y, Z and R$^{16}$ are as defined therein and R$^{11}$ and R$^{15}$ are each hydrogen.

4. A compound according to claim 3 wherein
Y is —O—,
Z is —(C1–C10-alkyl), aryl, heterocyclic or —NR$^{23}$R$^{24}$, wherein
R$^{23}$ and R$^{24}$ are independently selected from:
  (1) hydrogen,
  (2) aryl,
  (3) heterocyclic and
  (4) —(C1–C10-alkyl) optionally substituted with hydroxy, amino, aryl or heterocyclic, or, alternatively, —NR$^{23}$R$^{24}$ represents a 3- to 7-membered heterocyclic ring,
R$^{16}$ is
  (1) hydrogen,
  (2) —(C1–C10-alkyl) optionally substituted with hydroxy, amino, aryl or heterocyclic,
  (3) aryl or
  (4) heterocyclic,
and
R$^{11}$ and R$^{15}$ are each hydrogen.

5. A compound according to claim 4 wherein Y is —O— and Z is —CH$_3$ and R$^{11}$ and R$^{15}$ are each hydrogen.

6. A compound of the formula:

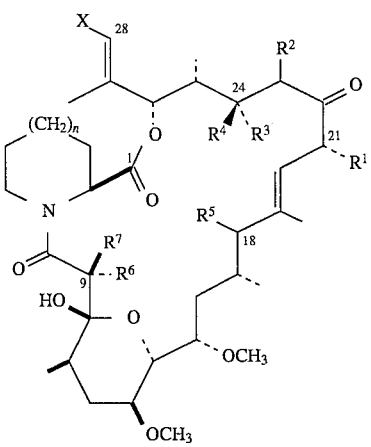

(II)

or a pharmaceutically acceptable salt, ester, amide or prodrug thereof wherein the ester is selected from C1-to-C6 alkyl esters, C5-to-C7 cycloalkyl esters, arylalky esters and esters which result from reaction of an alcohol moiety in the compound of formula II with C1-to-C6 carboxylic acids, C1-to-C6 dicarboxylic acids or aryl-carboxylic acids and wherein the amide results from reaction of a carboxylic acid moiety in the compound of formula II with $NH_3$, $NH_2$(C1–C6-alkyl), $NH$(C1–C6-alkyl)$_2$ or a 5, or 6-membered heterocycle containing one nitrogen atom and wherein the prodrug is selected from the group consisting of (a) acyloxymethyl esters of carboxylic acids, (b) (5-methyl-2-oxo-1,3-dioxolen-4-yl)methyl esters of carboxylic acids, (C) esters derived from alcohol groups in the parent drug by reaction with succinic acid, phosphoric acid, dialkylaminoacetic acid or an amino acid (d) N-Mannich bases of amides or amines, (e) N-hydroxymethyl derivatives of amides, (f) N-acyloxyalkyl derivatives of amides or heterocyclic amines, (g) oxazolidinone derived from ketone groups in the parent drug by reaction with 2-aminoethanol, N-methyl-2-aminoethanol, N-(2-hydroxyethyl)-2-aminoethanol, 2-aminopropanol, 2-amino, 2-methylpropanol, 2-amino-2-hydroxymethylpropanol, 3-amino-2-hydroxypropane, 2-amino-1-phenylethanol, 3-aminopropanol or N-methyl-2-amino-1-phenylpropanol and (h) enol esters derived from ketone groups in the parent drug, and (a) wherein n=1; $R^1$=Et; $R^2$=H; $R^3$=OH; $R^4$=H; $R^5$=H; $R^6$ and $R^7$ taken together=O; and X is

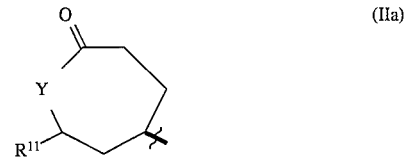

(IIa)

wherein Y=O; and $R^{11}$=H;

(b) wherein n=1; $R^1$=Et; $R^2$=H; $R^3$=OH; $R^4$=H; $R^5$=H; $R^6$ and $R^7$ taken together=O; and X is

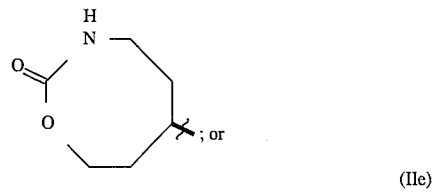

(IIe)

(c) wherein n=1; $R^1$=Et; $R^2$=H; $R^3$=OH; $R^4$=H; $R^5$=H; $R^6$ and $R^7$ taken together=O; and X is

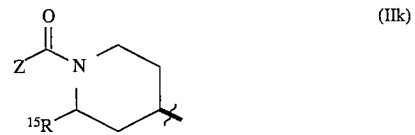

(IIk)

wherein Z=morpholin-1-yl; $R^{15}$=H;
or a pharmaceutically acceptable salt, ester, amide or prodrug thereof.

* * * * *